United States Patent [19]
Löfdahl et al.

[11] Patent Number: 5,100,788
[45] Date of Patent: Mar. 31, 1992

[54] METHOD OF PRODUCING AND ISOLATING IGG-BINDING PROTEIN A FUSION PEPTIDES AND A VECTOR THEREFOR

[75] Inventors: Sven Löfdahl; Mathias Uhlén; Martin Lindberg; John Sjöquist, all of Uppsala, Sweden

[73] Assignee: Pharmacia LKB Biotechnology AB, Uppsala, Sweden

[21] Appl. No.: 196,846

[22] Filed: May 9, 1988

Related U.S. Application Data

[63] Continuation of Ser. No. 667,492, filed as PCT/SE84/00046, Feb. 9, 1984, abandoned.

[30] Foreign Application Priority Data

Feb. 9, 1983 [SE] Sweden ................ 8300693

[51] Int. Cl.$^5$ ............ C12P 21/02; C12N 15/09; C12N 15/11; C12N 1/20
[52] U.S. Cl. .................... 435/69.7; 435/71.2; 435/91; 435/172.3; 435/252.3; 435/252.31; 435/252.33; 435/320.1
[58] Field of Search ............ 435/91, 172.3, 69.1, 435/79.1; 530/300, 350

[56] References Cited

U.S. PATENT DOCUMENTS

| | | | |
|---|---|---|---|
| 4,336,336 | 6/1982 | Silhavg et al. ............ | 435/172 |
| 4,338,397 | 7/1982 | Gilbert et al. ............ | 435/68 |
| 4,801,537 | 1/1989 | Nagarajan et al. ............ | 435/172.3 |
| 4,888,280 | 12/1989 | Palmer et al. ............ | 435/69.7 |
| 4,900,660 | 2/1990 | Boyle et al. ............ | 435/7 |
| 4,948,874 | 8/1990 | Kronvall et al. ............ | 530/350 |

FOREIGN PATENT DOCUMENTS

| | | |
|---|---|---|
| 8000030 | 1/1980 | PCT Int'l Appl. . |
| 2091268 | 7/1982 | United Kingdom . |
| 2091269 | 7/1982 | United Kingdom . |

OTHER PUBLICATIONS

Akerstrom et al. (1985), Journal of Immunology, vol. 135, pp. 2589-2592.
Reis et al. (1986), Molecular Immunology, vol. 23, pp. 425-433.
Umeda et al., J. Bacteriol. 141:838-844, 1980.
Lindmark et al., Eur. J. Biochem., 74:623-628, 1977.

*Primary Examiner*—Richard A. Schwartz
*Assistant Examiner*—Richard M. Lebovitz
*Attorney, Agent, or Firm*—Lowe, Price, LeBlanc & Becker

[57] ABSTRACT

A method of producing and selectively isolating a desired protein or polypeptide or derivative thereof by constructing a recombinant vector comprising a DNA sequence coding for said desired protein or polypeptide operatively linked to a DNA sequence coding for protein A or an active polypeptide fragment thereof or any other macromolecule capable of binding to the constant regions of immunoglobulins, such that said DNA sequences together code for an IgG-binding fusion product between said desired protein or polypeptide and said protein A, active polypeptide fragment thereof or macromolecule; transforming a compatible host with said recombinant vector such that the combined DNA sequences coding for said fusion protein or polypeptide can be expressed by the host, and culturing the transformed host in a suitable growth medium to produce said fusion protein or polypeptide; selectively isolating said fusion protein or polypeptide by adsorption to an IgG-supporting carrier material; and optionally desorbing said fusion protein or polypeptide from said IgG-supporting carrier, said fusion protein or polypeptide coded for by said combined DNA-sequence optionally comprising a unique cleavage site between said protein A part and said desired protein or polypeptide part, said desired protein or polypeptide part then being cleaved off from the rest of the fusion protein or polpeptide either while the latter is adsorbed to the IgG-supporting carrier or after desorption thereof from the carrier. Also a hybrid vector for use herein, a method and an expression vector for its preparation and a host organism transformed by said hybrid vector are disclosed.

20 Claims, 20 Drawing Sheets

```
TTCTATGAAATC TTGAACATGCCT AACTTAAACGAA GCGCAACGTAAC GGCTTCATTCAA AGTCTTAAAGAC        576
PheTyrGluIle LeuAsnMetPro AsnLeuAsnGlu AlaGlnArgAsn GlyPheIleGln SerLeuLysAsp
    110                                   120                        130
                                          Glu
                                                                        ┌──→A
GACCCAAGCCAA AGCACTAACGTT TTAGGTGAAGCT AAAAAATTAAAC GAATCTCAAGCA CCGAAAGCTGAT        648
AspProSerGln SerThrAsnVal LeuGlyGluAla LysLysLeuAsn GluSerGlnAla ProLysAlaAsp
                 140                                   150

AACAATTTCAAC AAAGAACAACAA AATGCTTTCTAT GAAATCTTGAAT ATGCCTAACTTA AACGAAGAACAA        720
AsnAsnPheAsn LysGluGlnGln AsnAlaPheTyr GluIleLeuAsn MetProAsnLeu AsnGluGluGln
                 160                                   170
                        HindIII
CGCAATGGTTTC ATCCAAAGCTTA AAAGATGACCCA AGCCAAAGTGCT AACCTATTGTCA GAAGCTAAAAAG        792
ArgAsnGlyPhe IleGlnSerLeu LysAspAspPro SerGlnSerAla AsnLeuLeuSer GluAlaLysLys
 180                                       190                          Ala 200
                                                    ┌──→B
TTAAATGAATCT CAAGCACCGAAA GCGGATAACAAA TTCAACAAAGAA CAACAAAATGCT TTCTATGAAATC        864
AsnGluSer GlnAlaProLys AlaAspAsnLys PheAsnLysGlu GlnGlnAsnAla PheTyrGluIle
    210                                                    220
```

FIG. 3B

```
TTACATTTACCT  AACTTAAACGAA  GAACAACGCAAT  GGTTTCATCCAA  AGCCTAAAAGAT  GACCCAAGCCAA      936
LeuHisLeuPro  AsnLeuAsnGlu  GluGlnArgAsn  GlyPheIleGln  SerLeuLysAsp  AspProSerGln
    230                         240                         250

AGCGCTAACCTT  TTAGCAGAAGCT  AAAAAGCTAAAT  GATGCTCAAGCA  CCAAAAGCTGAC  AACAAATTCAAC     1008
SerAlaAsnLeu  LeuAlaGluAla  LysLysLeuAsn  AspAlaGlnAla  ProLysAlaAsp  AsnLysPheAsn
                   260                         270                         Asn
                                                             ┌──→C

AAAGAACAACAA  AATGCTTTCTAT  GAAATTTTACAT  TTACCTAACTTA  ACTGAAGAACAA  CGTAACGGCTTC     1080
LysGluGlnGln  AsnAlaPheTyr  GluIleLeuHis  LeuProAsnLeu  ThrGluGluGln  ArgAsnGlyPhe
                   280                         290

ATCCAAAGCCTT  AAAGACGATCCT  TCGGTGAGCAA  GAAATTTTAGCA  GAAGCTAAAAAG  CTAAACGATGCT      1152
IleGlnSerLeu  LysAspAspPro  SerValSerLys  GluIleLeuAla  GluAlaLysLys  LeuAsnAspAla
    300                         310                         320

CAAGCACCAAAA  GAGGAAGACAAT  AACAAGCCTGGC  AAAGAAGACAAT  AACAAGCCTGGC  AAAGAAGACAAT     1224
GlnAlaProLys  GluGluAspAsn  AsnLysProGly  LysGluAspAsn  AsnLysProGly  LysGluAspAsn
                   330                         340
     ┌──→X

AACAAGCCTGGG  AAAGAAGACAAC  AACAAGCCTGGC  AAAGAAGACAAC  AACAAGCCTGGT  AAAGAAGACAAC     1296
AsnLysProGly  LysGluAspAsn  AsnLysProGly  LysGluAspAsn  AsnLysProGly  LysGluAspAsn
    350                         360                         370

AACAAGCCTGGC  AAAGAAGACGGC  AACAAGCCTGGT  AAAGAAGACAAC  AAAAAACCTGGT  AAAGAAGATGGC     1368
AsnLysProGly  LysGluAspGly  AsnLysProGly  LysGluAspAsn  LysLysProGly  LysGluAspGly
                   380                         390
```

FIG. 3C

```
AACAAGCCTGGT AAAGAAGACAAC AAAAAACCTGGT AAAGAAGACGGC AACAAGCCTGGC AAAGAAGATGGC    1440
AsnLysProGly LysGluAspAsn LysLysProGly LysGluAspGly AsnLysProGly LysGluAspGly
                          400                       410

AACAAACCTGGT AAAGAAGATGGT AACGGAGTACAT GTCGTTAAACTT GGTGATACAGTA AATGACATTGCA    1512
AsnLysProGly LysGluAspGly AsnGlyValHis ValValLysLeu GlyAspThrVal AsnAspIleAla
420                                    430                                   440

PatI                                            BalI
AAAGCAAACGGC ACTACTGCTGAC AAAATTGCTGCA GATAACAAATTG GCTGATAAAAAC ATGATCAAACTT    1584
LysAlaAsnGly ThrThrAlaAsp LysIleAlaAla AspAsnLysLeu AlaAspLysAsn MetIleLysLeu
                          450                                   460

GGTCAAGAACTT GTTGTTGATAAG AAGCAACCACAA ACCATGCAGAGC TAACAAAGCTCA AGCATTATCAGA    1656
GlyGlnGluLeu ValValAspLys LysGlnProGln ThrMetGlnSer ***
470                                    490

AACTGGGAAGA AAATCCATTCAT CGGTACAACTGT ATTGGTGGATT ATCATTAGCCTT AGGTGCAGCGTT      1728

EcoRV
ATTAGCTGGACG TCGTCGCGAACT ATAAAAACAAAC AATACACAACGA TAGATATC                      1784
```

FIG. 3D

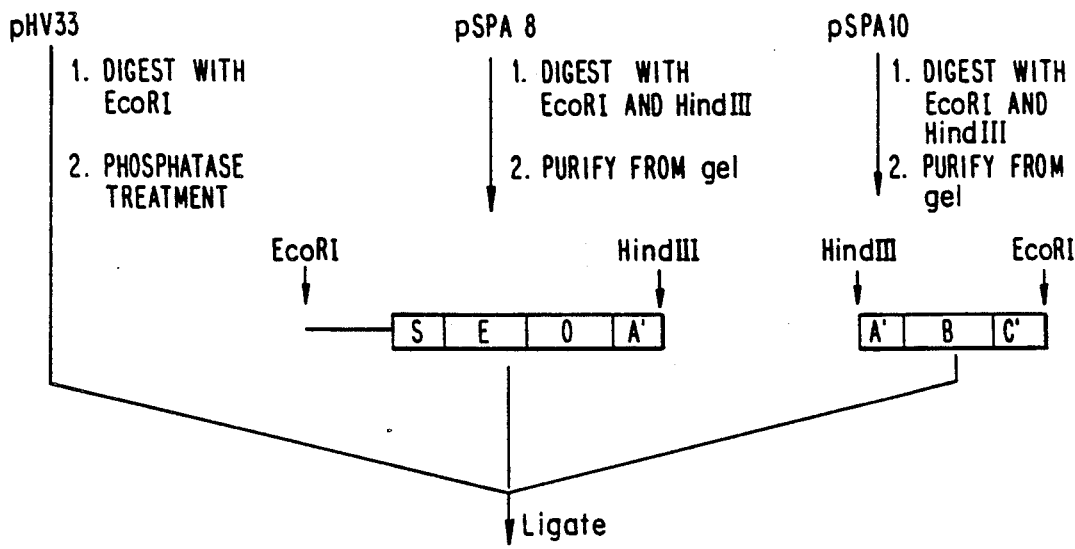
FIG. 8
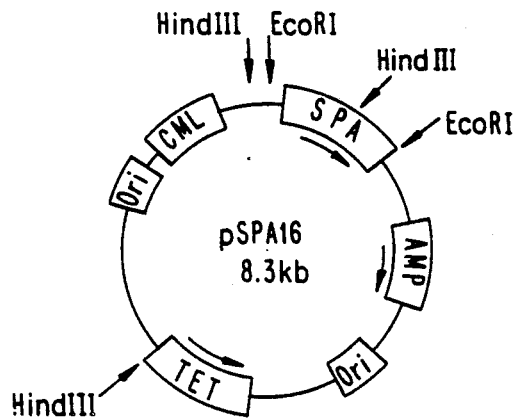
... AAA GAC GAT CCG GGG AAT TCT TGA ...
... Lys Asp Asp Pro Gly Asn Ser ***
268
FIG. 9

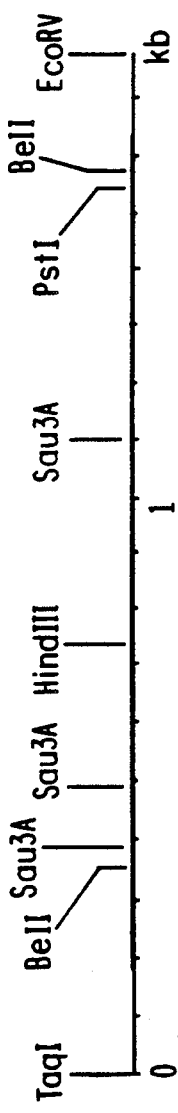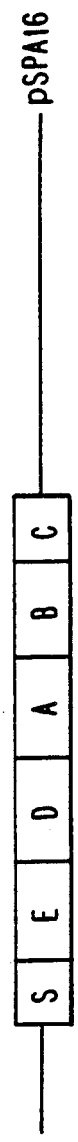
FIG. 10(A)
FIG. 10(B)
FIG. 10(C)

```
      1069           1081           1093           1105           1117
       |              |              |    Sau3A     |              |
      AACGGCTTCATC CAAAGCCTTAAA GACGATCCTTCG GTGAGCAAAGAA ATTTTAGCAGAA
      AsnGlyPheIle GlnSerLeuLys AspAspProSer ValSerLysGlu IleLeuAlaGlu 1513           1525           1537           1549           1561
       |              |              |    PstI      |              |
      GCAAACGGCACT ACTGCTGACAAA ATTGCTGTGCAGAT AACAAATTGGCT GATAAAAACATG
      AlaAsnGlyThr ThrAlaAspLys IleAlaAlaAsp AsnLysLeuAla AspLysAsnMet
```

FIG. 12

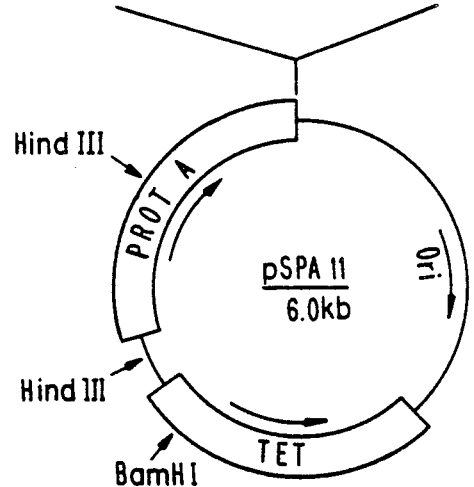
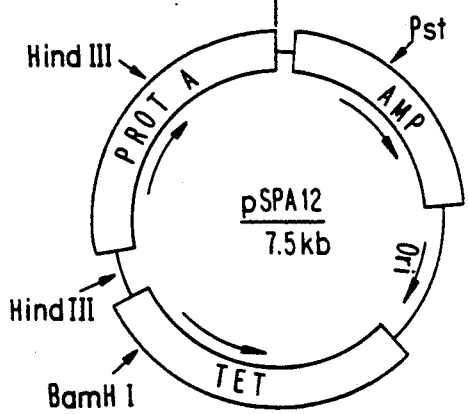
FIG. 13(A)  FIG. 13(B)
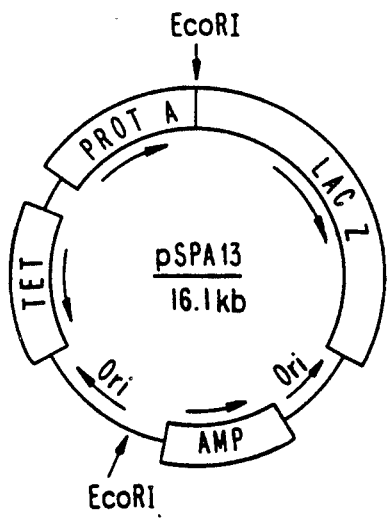
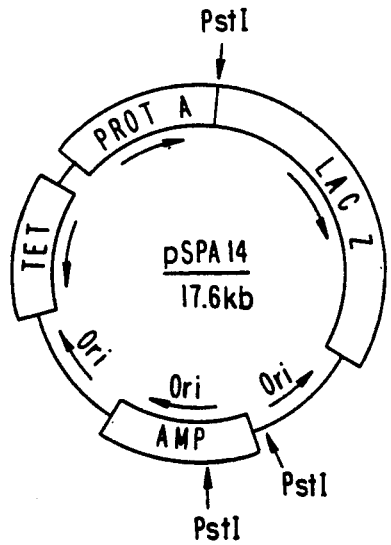
FIG. 14(A)  FIG. 14(B)

```
⎧ GCGCAACACGATGAAGCTCAACAAAATGCTTTTTATCAAGTCTTAAATATGCCTAACTTAAATGCTGATCAA      72
│ AlaGlnHisAspGluAlaGlnGlnAsnAlaPheTyrGlnValLeuAsnMetProAsnLeuAsnAlaAspGln
│
│ CGCAATGGTTTTATCCAAAGCCTTAAAGATGATCCAAGCCAAAGTGCTAACGTTTTAGGTGAAGCTCAAAAA      144
│ ArgAsnGlyPheIleGlnSerLeuLysAspAspProSerGlnSerAlaAsnValLeuGlyGluAlaGlnLys          -
│
│ CTTAATGACTCTCAAGCTCCAAAAGCTGATGCGCAACAAAATAACTTCAACAAAGATCAACAAAGCGCCTTC      216.
│ LeuAsnAspSerGlnAlaProLysAlaAspAlaGlnGlnAsnAsnPheAsnLysAspGlnGlnSerAlaPhe
│
│ TATGAAATCTTGAACATGCCTAACTTAAACGAAGCGCAACGTAACGGCTTCATTCAAAGTCTTAAAGACGAC      288
│ TyrGluIleLeuAsnMetProAsnLeuAsnGluAlaGlnArgAsnGlyPheIleGlnSerLeuLysAspAsp
│
│ CCAAGCCAAAGCACTAACGTTTTAGGTGAAGCTAAAAAATTAAACGAATCTCAAGCACCGAAAGCTGATAAC      360
│ ProSerGlnSerThrAsnValLeuGlyGluAlaLysLysLeuAsnGluSerGlnAlaProLysAlaAspAsn
│
│ AATTTCAACAAAGAACAACAAAATGCTTTCTATGAAATCTTGAATATGCCTAACTTAAACGAAGAACAACGC      432
│ AsnPheAsnLysGluGlnGlnAsnAlaPheTyrGluIleLeuAsnMetProAsnLeuAsnGluGluGlnArg
│
│ AATGGTTTCATCCAAAGCTTAAAAGATGACCCAAGCCAAAGTGCTAACCTATTGTCAGAAGCTAAAAAGTTA      504
│ AsnGlyPheIleGlnSerLeuLysAspAspProSerGlnSerAlaAsnLeuLeuSerGluAlaLysLysLeu
│
│ AATGAATCTCAAGCACCGAAAGCGGATAACAAATTCAACAAAGAACAACAAAATGCTTTCTATGAAATCTTA      576
│ AsnGluSerGlnAlaProLysAlaAspAsnLysPheAsnLysGluGlnGlnAsnAlaPheTyrGluIleLeu         •
│
│ CATTTACCTAACTTAAACGAAGAACAACGCAATGGTTTCATCCAAAGCCTAAAAGATGACCCAAGCCAAAGC      648
│ HisLeuProAsnLeuAsnGluGluGlnArgAsnGlyPheIleGlnSerLeuLysAspAspProSerGlnSer
⎨
│ GCTAACCTTTTAGCAGAAGCTAAAAAGCTAAATGATGCTCAAGCACCAAAAGCTGACAACAAATTCAACAAA      720
│ AlaAsnLeuLeuAlaGluAlaLysLysLeuAsnAspAlaGlnAlaProLysAlaAspAsnLysPheAsnLys
│
│ GAACAACAAAATGCTTTCTATGAAATTTTACATTTACCTAACTTAACTGAAGAACAACGTAACGGCTTCATC      792
│ GluGlnGlnAsnAlaPheTyrGluIleLeuHisLeuProAsnLeuThrGluGluGlnArgAsnGlyPheIle
│                                                         EcoRI
│ CAAAGCCTTAAAGACGATCCGGGGAATTCTATGGATCCCGAAACTCTGTGCGGTGCTGAACTGGTTGACGCT      864
│ GlnSerLeuLysAspAspProGlyAsnSerMetAspProGluThrLeuCysGlyAlaGluLeuValAspAla
│
│ CTGCAGTTTGTTTGCGGTGACCGTGGTTTTTATTTTAACAAACCCACTGGTTATGGTTCTTCTTCTCGTCGT      936
│ LeuGlnPheValCysGlyAspArgGlyPheTyrPheAsnLysProThrGlyTyrGlySerSerSerArgArg
│
│ CGTCCCCAGACTGGTATTGTTGACGAATGCTGCTTTCGTTCTTGCGACCTGCGTCGTCTGGAAATGTATTGC     1008
│ AlaProGlnThrGlyIleValAspGluCysCysPheArgSerCysAspLerArgArgLeuGluMetTyrCys
│                   HindIII
│ CGTCCCCTGAAACCCGCTAAATCTGCTTAGAAGCTT                                          1044
⎩ AlaProLeuLysProAlaLysSerAla***
```

FIG. 19

```
         A1           A2              A3              A4              A5
5' GGAATTCT ATGGGTCCCGAAAC TCTGTGCGGTGCTG AACTGGTTGACGCT CTGCAGTTTGTTTG
3' CCTTAAGATACCCA GGGCTTTGAGACAC GCCACGACTTGACC AACTGCGAGACGTC
         B17            B16             B15             B14

A6            A7          A8          A9
            CGGTGACCGTGGTT TTTATTTTAACAAA CCCACTGGTTATGG TTCTTCTTCTCGTC
AAACAAACGCCACT GGCACCAAAAATAA AATTGTTTGGGTGA CCAATACCAAGAAG AAGAGCAGCACGAG
       B13            B12            B11            B10           B9

A10           A11           A12          A13
GTGCTCCCCAGACT GGTATTGTTGACGA ATGCTGCTTTCGTT CTTGCGACCTGCGT
    GGGTCTGACCATAA CAACTGCTTACGAC GAAAGCAAGAACGC TGGACGCAGCAGAC
           B8            B7             B6            B5

A14           A15           A16           A17    3'
CGTCTGGAAATGTA TTGCGCTCCCCCTGA AACCCGCTAAATCT GCTTAGAAGCTTGG
    CTTTACATAACGCG AGGGGACTTTGGGC GATTTAGACGAATC TTCGAACC 5'
           B4             B3             B2            B1
```

FIG. 21A

METHOD OF PRODUCING AND ISOLATING IGG-BINDING PROTEIN A FUSION PEPTIDES AND A VECTOR THEREFOR

This application is a continuation of application Ser. No. 667,492, filed as PCT/SE84/00046, Feb. 9, 1984, now abandoned.

The present invention relates to a method of preparing protein and polypeptide products with high purity through recombinant DNA technology, and more particularly to the utilization of such technology to prepare novel gene products comprising desired proteins or polypeptides, which novel gene products are easily refinable, and optionally converting such gene products into the desired proteins or polypeptides. The invention also relates to such novel gene products.

The relatively new recombinant DNA technology or so-called genetic engineering, whereby novel recombinant DNA structures may be constructed from DNA segments derived from different biological sources and introduced into a prokaryotic or eukaryotic host cell to produce the corresponding protein or polypeptide, has made it possible to produce a great number of proteins which can otherwise only be obtained from natural sources and at considerable costs. Well-known examples are insulin and the growth hormone somatostatin. The proteins produced by the host cells are either trapped within the cells or secreted into the surrounding growth medium. In the former case the cells must be ruptured to permit the desired protein to be isolated, whereas in the latter case it can be separated from the growth medium. Even in case of secreted proteins, however, the preparation from which the protein is to be isolated is relatively complex containing a variety of other substances, and despite efficient separation techniques both the purity and yield of the desired protein may be low.

The present invention provides a solution to the above mentioned problem through a method based upon recombinant DNA technology which permits desired proteins and polypeptides to be produced with extreme purity. According to the invention this is achieved by utilizing the unique binding properties of protein A from Staphylococci in combination with gene fusion technology as will be explained below.

Protein A is known as a cell wall component of the bacterium *Staphylococcus aureus*, hereinafter called *S. aureus*, and it is characterized by a specific serological reaction with mammal immunoglobulins. In contrast to the normal antigen-antibody reactions, however, protein A binds to the Fc-portion of all subclasses of human immunoglobulins type G, or IgG, except $IgG_3$, leaving the Fab-portion thereof free for antigen and hapten coupling. This property has given protein A a widespread use in both quantitative and qualitative immunochemical techniques. Covalently bound to a carrier protein A is thus an excellent immunosorbent for the isolation of IgG. The exact structure of protein A may vary depending on its origin. It has a molecular weight of about 42,000 and a markedly extended shape. The N-terminal part of the molecule comprises four or five highly homologous IgG-binding units, while the C-terminal part lacks Fc-binding ability. As used in the following description and claims, the term "protein A" is, however, not restricted to the above defined staphylococal protein, but means any macromolecule having analogous immunological and biological activities to the protein A produced by staphylococci, such as the natural strains of *S. aureus*, including any mutants thereof. Similarly "active fragments of protein A" or "active derivatives of protein A" are meant to comprise any polypeptide fragments or derivatives, respectively, of protein A as well as oligomeric forms of immunoreactive macromolecules or active fragments thereof or other macromolecules that are capable of binding to the constant regions of at least one immunoglobulin.

In our International patent application PCT/SE83/00297 (Swedish patent application No. 8204810-9) corresponding to U.S. Ser. No. 601,630, the disclosures of which are incorporated herein by reference, the isolation and characterization of the gene coding for staphylococcal protein A as well as the expression thereof in *Escherichia coli*, hereinafter called *E. coli*, are described. An *E. coli* strain transformed with a plasmid containing this staphylococcal protein A gene has been deposited on July 12, 1982 with the Deutsche Sammlung von Mikroorganismen (DSM), Göttingen, Federal Republic of Germany, under No. DSM 2434. By using, e.g., this protein A gene containing plasmid, named pSPA1, protein A genetic material for the purposes of the present invention may be obtained.

It is assumed that the specific terms relating to gene technology, which will be used in the following description and claims, are well-known and accepted in the art. Definitions of a selection thereof may, however, be found in, for example, the above mentioned International patent application PCT/SE83/00297.

Gene fusion is a procedure wherein the coding sequence of two or more genes are spliced together to form a combined gene which on expression in a suitable host organism will produce a fusion product wherein the separate proteins or polypeptides coded for by the respective genes are fused together into a single molecule. The gene fusion technique is of growing importance and has so far been used to study various biological problems, such as protein transport mechanisms, plasmid replication and gene expression. Extensive use in this respect has been made of especially the *E. coli* lac Z gene coding for the enzyme $\beta$-galactosidase.

In accordance with the present invention gene fusion is used to combine a first DNA-sequence coding for protein A or an active polypeptide fragment thereof with a second DNA-sequence coding for a desired protein or polypeptide into a functional gene capable of expressing the fusion product of said desired protein or polypeptide and the protein A component. Due to the IgG-binding ability of the protein A part, the produced protein or polypeptide can easily be isolated with high efficiency by conventional affinity chromatography utilizing immunoglobulin of type IgG immobilized to a suitable carrier. The carrier-bound fusion product may be used as such, e.g. if the desired protein is an enzyme, or it may be released from the carrier, either as a whole including the protein A part, or only the desired protein or polypeptide part thereof through cleavage with a suitable agent as will be further described below.

A basic aspect of the present invention is thus the provision of a recombinant DNA cloning vehicle or vector comprising a DNA sequence coding for a desired protein or polypeptide operatively linked to a DNA sequence coding for protein A or an active polypeptide fragment thereof, such that said DNA sequences together code for an IgG-binding fusion product of said desired protein or polypeptide and said protein A or active polypeptide fragment thereof. In order to be capable of transforming (which is also meant to include the case that the vector is a bacteriophage) a host organism to produce said fusion product, the vector in conventional manner further comprises a replicon and a promoter for the combined fusion product coding DNA sequence. For purposes which will be further elucidated below said combined DNA sequence may comprise a sequence coding for an appropriate cleavage site between the DNA sequences coding for the desired protein and protein A, respectively, such that the protein A part of the fusion molecule may be cleaved off as mentioned above. A more detailed description of the recombinant vector according to this aspect of the invention as well as the construction thereof will be described in more detail further on.

By transforming a compatible host organism with said vector to permit expression of the above combined DNA sequence and culturing the host in a nutrient medium the corresponding IgG-binding fused protein or polypeptide will be produced. Although bacterial hosts, such as strains of, for example, Escherichia, Bacillus and Staphylococcus, are preferred for the purposes of the invention, it is, of course, also within the scope thereof to use other hosts, such as yeasts and other fungi, plant cells in culture, etc. The transformation of the hosts may be effected with well-known methods.

Due to IgG-binding ability of the protein A moiety of the fusion molecule produced by the cultured hostorganism the fusion molecule can be very efficiently isolated from the cell culture by means of IgG immobilized to a suitable carrier. If the fusion product is secreted into the surrounding medium the binding to the carrier may be performed directly from the medium. If, on the other hand, the fusion product remains within the cells the latter have to be ruptured before such immunosorbance can be effected. Rupture of the cell walls may be effected in conventional manner by, e.g., high pressure, ultrasonication, homogenization, shaking with glass-beads etc. In cases where the product is trapped within the periplasmic space between two cell membranes, as in gram-negative bacteria, an osmotic shock procedure may be used to release the product into the suspension medium. Any other treatment of the cultured cells or the growth medium prior to the IgG-aided isolation of the fusion product is, of course, also within the scope of the invention.

In conventional manner the immobilization process may be performed batch-wise with the IgG-coupled carrier slurried in a suitable medium, or on a column of the activated carrier. IgG-coupled carriers for chromatographic use, e.g. IgG-Sepharose ® (Pharmacia AB, Sweden) are commercially available and may advantageously be used for the purposes of the invention. However, any conventional carrier material to which IgG can be sufficiently coupled for the present purposes may be used. The methods for coupling or immobilizing IgG to such carrier materials is well-known and need not be described in any detail herein. Sepharose ® is a high molecular weight cross-linked polysaccharide which is useful in gel filtration for the separation of macromolecules.

Release or desorption of the fused protein or polypeptide which is bound to the IgG-carrier may be effected by conventional methods, such as lowering the pH, e.g. by means of glycine buffer (pH 3.0), treatment with high salt concentrations or chaotrophic ions, or by competitive elution using excess soluble protein A or IgG or fragments thereof to displace the fusion protein or polypeptide from the IgG-carrier adsorbent. The choice of desorption method should, of course, be made with regard to the particular desired protein or polypeptide, such that a desired activity thereof is not lost or considerably reduced thereby. From the resulting eluate the fusion protein or polypeptide may readily be isolated and, if desired, subjected to further purification steps, such as gel filtration, ion exchange etc.

The purified fusion protein or polypeptide obtained may in itself be a valuable product as will be described below, and another aspect of the present invention is therefore the provision of a method of producing a highly purified fused protein or polypeptide product comprising the steps of transforming a compatible host with the above vector, culturing said host in a nutrient medium, isolating said fused protein or polypeptide from said host culture by selective binding thereof to an IgG-supporting carrier, and optionally releasing the fused protein or polypeptide from the carrier, as well as such an isolated fused product obtained thereby.

One valuable use of such a fusion product is when the protein fused to the protein A part is an enzyme. In such cases the IgG-binding activity of the fusion product is utilized for immobilizing the enzyme to a carrier material having IgG coupled thereto. Such an enzyme system offers several advantages. Since the enzyme is bound to the carrier via the protein A-IgG coupling, all the enzyme molecules will be bound to the carrier in exactly the same way and maximum activity thereof will thus be obtained. When the enzyme activity has decreased to an unacceptably low level, such a system can easily be regenerated by conventionally desorbing the enzyme from the carrier through a pH change, e.g. glycine buffer treatment, and then binding fusion product containing active enzyme thereto. The binding or adsorption of the fused enzyme in question to the IgG-coupled carrier may be effected either directly from the appropriately pretreated cells or cell medium, or in purified state after adsorption and desorption from another IgG-coupled adsorbent.

Immobilization of enzymes as above may be applied to such enzyme systems which are already used industrially as well as to enzyme systems not yet commercialized, as long as the DNA fragment coding for the selected enzyme is available. As examples of such enzyme systems may be mentioned amino-acid acylase, glucose-isomerase, penicillin-amidase, aspartase, fumarase, $\beta$-galactosidase, alkaline phosphatase, etc.

Another case when the IgG-binding ability of the fused protein or polypeptide is desirable is, for example, for providing certain protein A conjugates which may be used in the well-known variant of immuno-chemical analysis named ELISA (enzyme linked immunosorbent assay). Two examples of such conjugates, which are frequently used and also are commercially available, are $\beta$-galactosidase and alkaline phosphatase. When these conjugates are prepared in conventional manner, i.e. by chemically binding protein A to the respective enzyme, only part of the two components will be correctly bonded to each other, the resulting conjugate mixture thus containing a relatively high proportion of inactive or poorly active conjugates. In contrast thereto, the corresponding conjugates prepared according to the present invention in the form of a fused gene product will always have the correct coupling relationship between protein A and the enzyme and consequently always maximum and definable activity.

Still another case when the fused protein or polypeptide obtained may be used is when the protein A residue thereof does not inactivate or otherwise prevent the intended use of the desired protein or polypeptide fused to the protein A part. In such a case the fusion product may well be used instead of the respective pure protein or polypeptide, and it will thus not be necessary to cleave off the protein A part therefrom as will be described below as a further aspect of the invention.

The protein part of the fused protein or polypeptide may under certain conditions be cleaved off, the pure desired protein or polypeptide thereby being obtained. In another aspect the present invention therefore provides a method of producing a desired protein or polypeptide of high purity comprising the steps of transforming a compatible host with the above mentioned vector, culturing said host in a nutrient medium, isolating said fused protein or polypeptide from the cell culture by selective binding to an IgG-supporting carrier, and cleaving off the desired protein or polypeptide from the protein A part of said fused protein or polypeptide, either directly from the carrier bound fusion product or after desorption thereof from the carrier.

A necessary condition to permit such cleavage of the fused protein or polypeptide is, of course, that it contains a unique cleavage site which may be recognized and cleaved by suitable means. Such a cleavage site may be a unique amino-acid sequence recognizable by chemical or enzymatic means and located between the desired protein or polypeptide and protein A sections, respectively, of the fused product to be produced. Such a specific amino acid sequence must not occur within the desired protein or polypeptide and preferably not in the protein A part of the fusion product. Examples of enzymatic agents include proteases, such as collagenase, which in some cases recognizes the amino acid sequence $NH_2$—Pro—X—Gly—Pro—COOH, wherein X is an arbitrary amino acid residue, e.g. leucine; chymosin (rennin), which cleaves the Met-Phe bond; kallikrein B, which cleaves on the carboxyl side of Arg in X—Phe—Arg—Y; enterokinase, which recognizes the sequence X—$(Asp)_n$—Lys—Y, wherein n=2-4, and cleaves it on the carboxyl side of Lys; thrombin which cleaves at specific arginyl bonds. Examples of chemical agents include cyanogen bromide (CNBr), which cleaves after Met; hydroxylamine, which cleaves the Asn-Z bond, wherein Z may be Gly, Leu or Ala; formic acid, which in high concentration (~70%) specifically cleaves Asp-Pro. Thus, if the desired protein or polypeptide does not contain any methionine sequences, which is the case for, e.g., the hormone somatostatin, the cleavage site may be a methinonine group which can be selectively cleaved by cyanogen bromide. Often it may be preferred to use chemical cleaving agents because protease recognition sequences may be sterically hindered in the produced fused protein. The techniques for introducing the corresponding DNA sequences coding for such cleavage susceptible peptide units or residues into the DNA sequence coding for the fused protein or polypeptide are well-known per se in the art and need not be discussed in any detail herein. In case a specific cleavage sequence which does not occur in the desired protein, occurs in the protein A molecule, this amino acid sequence may, without changing the activity of the protein A part, be converted into sequences which are not recognized and cleaved by the particular cleavage means by methods known per se in the art.

As mentioned above the cleavage may be effected either with the fusion product bound to the IgG-coupled carrier or after desorption therefrom. A batch-wise procedure may be carried out as follows. The carrier, e.g. IgG-Sepharose ® (Pharmacia AB, Sweden) having the fusion protein or polypeptide bound thereto is washed with a suitable medium and then incubated with the cleaving agent, such as protease or cyanogen bromide. After separation of the carrier material having the protein A residue bound thereto, a solution containing the desired protein or polypeptide and the cleavage agent is obtained, from which the former may be isolated and optionally further purified by conventional techniques such as gel filtration, ion-exchange etc.

In case of the carrier being in column form and the fusion protein or polypeptide comprising a protease recognition site, the cleavage procedure may be performed in the following way. The column of carrier having the fusion protein or polypeptide bound thereto is washed with a suitable medium, and then eluted with an appropriate agent which is gentle to the desired protein or polypeptide to be produced as mentioned hereinbefore. Such an agent may, depending on the particular protein or polypeptide, be a pH-lowering agent, such as, e.g. a glycine buffer, or a protein A solution (competitive elution). The eluate, containing the pure fusion protein or polypeptide together with the cleavage agent, is then passed through a second column comprising the immobilized protease, e.g. collagenase when the cleavage site is a collagenase susceptible sequence. When passing therethrough the fusion protein or polypeptide is cleaved into the desired protein or polypeptide and a protein A residue. The resulting solution is then passed through the same or another IgG-coupled column than used above, whereby the protein A component of the solution is adsorbed and the resulting through-flow is a pure solution of the desired protein or polypeptide. When the desorption agent is a protein A solution, the protein A adsorbed in the last step may be eluted and recycled to cleavage solution, the system then being a regenerative system with respect to protein A.

By means of the above aspect of the present invention a desired protein or polypeptide may readily be obtained with extreme purity and high yields using only a small number of process steps. Such highly purified forms of desired proteins and polypeptides are, for example, excellently suited for the production of antibodies through immunisation of an animal, such as rabbit. Another possible application is the combination thereof with the so-called hybridoma technique for the production of monoclonal antibodies.

Desired proteins and polypeptides which can be produced with extreme purity in accordance with the present invention aspect are, for example, enzymes, such as various oxido-reductases, transferases, hydrolases, lyases, isomerases and ligases; hormones, such as parathyroid hormones, growth hormone, gonadotropins (FSH, luteinizing hormone, chorionogonadotropin and glycoproteins), insulin, ACTH, somatostatin, prolactin, placental lactogen, melanocyte stimulating hormone, thyrotropin, parathyroid hormone, calcitonin, enkephalin and angiotensin; and other proteins, such as serum proteins, fibrinogen, fibronectin, prothrombin, thromboplastin, globulin, e.g. gammaglobulins or anti-bodies, heparin, coagulation factors, complement factors, plasma proteins, oxytocin, albumins, actin, myosin, hemoglobin, ferritin, cytochrome, myoglobin, lactoglobulin, histones, avidin, thyroglobulin, interferon, transcortical kinins, etc., and as suggested above peptide antigens for use in making vaccines.

As appears from the above a crucial part of the present invention is the provision of the recombinant DNA structure or vector comprising the combined gene coding for the present fusion protein or polypeptide and capable of transforming a host cell to permit expression thereof and production of the fusion product. The present invention is meant to encompass any such vector irrespective of how it has been obtained using, for example, various restriction enzyme cutting, ligating, transforming and screening techniques well-known in the art as well as any appropriate vector materials and host-organisms. Thus, the DNA sequence coding for the desired protein or polypeptide may be inserted into a suitable vector and the protein A coding DNA sequence inserted subsequently, or vice versa; or the two DNA sequences may be introduced simultaneously into the vector. It is also possible to insert the respective DNA sequences in parts thereof into the vector. Further the two DNA sequences may be arranged with either the protein A coding sequence or the sequence coding for the desired protein or polypeptide at the 5'-end or start of the combined gene. The special techniques for accomplishing such insertions and combinations with maintained correct reading frames, including the provision of suitable restriction sites therefore, are well-known per se in the art.

The source of the DNA sequence coding for protein A or an active polypeptide thereof may be any structure from which the corresponding gene or DNA-segment may be obtained such as a protein A gene containing plasmid. A suitable source is, for example, one of the protein A gene containing plasmids pSPA1, pSPA3 and pSPA5 as constructed and described in our International patent application PCT/SE83/00297 (Swedish patent application 8204810-9). From such a vector the whole or an appropriate part of the protein A gene may be cut out with suitable restriction enzymes corresponding to suitably located restriction sites in or close to the gene. The extent of the protein A gene to be included in the combined gene coding for the fusion product should be sufficient for imparting IgG-binding activity to the fusion product, which usually means at least a major part of the gene segment coding for the IgG-binding part of the protein A molecule. As will appear from the experimental part below, it may, however, at least in certain cases, be favourable to also include at least part of the gene segment coding for the non-IgG-binding part of the molecule. This part of the molecule will then serve as a spacer between the IgG-active part and the desired protein part of the fusion product.

The source of the DNA sequence coding for the desired protein or polypeptide, which may be of prokaryotic as well as eukaryotic origin, may likewise be any structure from which a corresponding gene or gene segment may be obtained. A suitable source is a plasmid containing such a gene or gene segment. From such a plasmid an appropriate part of the gene in question, i.e. that codes for a sufficient part of the corresponding protein or polypeptide to have the desired activity, may be cut out with suitable restriction enzymes corresponding to suitably located restriction sites in or close to the gene.

The origin of the vector part of the recombinant vector of the invention is preferably a plasmid but it may also be of viral or phage origin. The particular choice of vector depends on the host-organism to be transformed. As mentioned above the latter may be selected from bacteria, fungi, plants and algae. The preferred host is, however, bacteria, and bacteria susceptible to transformation comprise, e.g. members of Enterobacteriaceae, such as strains of *E. coli* and Salmonella, Bacillaceae, such as *Bacillus subtilis*, Pneumococcus, Streptococcus, Staphylococcus, Micrococcus and Hemophilus.

When constructing a recombinant DNA vector of the invention it is preferable to first construct an expression or fusion vector comprising a functional DNA sequence coding for protein A or an active polypeptide fragment thereof, and at least one unique restriction site at or near the end of the protein A coding gene. Such a fusion vector may be constructed by providing a suitable vector, e.g. a plasmid vector, containing the whole or a sufficient part of the protein A coding gene as discussed above. A unique restriction site, or preferably a multilinker containing several different restriction sites, is then inserted into the protein A gene after the IgG-binding region but before the stop codon. Such an insertion may, as will appear from the following experimental part, be effected in several steps and plasmids. The resulting fusion vector may then be used for insertion of any DNA sequence coding for a desired protein or polypeptide. Such a fusion vector is also part of the present invention.

To insert a DNA sequence coding for a desired protein or polypeptide into the fusion vector, it is preferably provided as part of a plasmid. If suitable restriction sites giving complementary ends to those obtained when cutting the fusion vector in one of the unique restriction sites are not present in the gene, such sites may be inserted by conventional methods. They should be inserted as far upstream as possible, i.e. near the 5'-end, in the gene or before the start codon provided that there is no stop codon in -between. By cleaving the fusion vector and the desired gene containing plasmid at the appropriate restriction sites and ligating the mixture, a recombinant vector containing the combined gene may be obtained. Although it may be preferred to cut out the gene coding for the desired protein and insert it into the plasmid, it is also possible to cut the plasmid only at the start of the gene and combine the two plasmids. The above is, however, only a rough example and many variations are possible.

To provide a recombinant vector coding for a fusion protein or polypeptide from which the protein A part may be cleaved off, a synthetic sequence coding for an oligopeptide, which can be recognized by a protease or a peptide cleaving chemical agent, may be inserted between the two fused genes or gene segments. Such insertions may be performed with conventional methods. A proviso is, of course, that the fusion protein or polypeptide, or at least not the desired protein, does not contain other peptide sequences that may be cleaved by the protease or chemical agent.

For the case that a gram-positive bacterium, such as *Bacillus subtilis* or any staphylococcal species, is to be transformed by the recombinant vector, the control regions of the protein A gene (promoter and ribosome binding sequence) may advantageously be used. For gram-negative bacteria, such as *E. coli*, it may be preferable to insert a control region of such origin, e.g. from the *E. coli* phage lambda.

Apart from the fact that the control regions of the protein A gene function well in gram-positive bacteria, these hosts having a single membrane are favourable from another point of view, viz. that the signal peptide, coded for by the signal sequence of the protein A gene, may serve to secrete the fusion protein or polypeptide into the surrounding medium. In a gram-negative bacterium, such as *E. coli*, the fusion product will be trapped between the two cell-membranes. Secretion of the product offers great advantges in that the cells need not be ruptured for recovery of the product but can readily be separated and the fusion protein or polypeptide be adsorbed directly from the medium.

As is well-known foreign proteins produced by recombinant DNA techniques in *E. coli* may be subjected to proteolytic degradation of the product. Such degradation may be minimized by using a temperature-sensitive repressor which is inactivated at higher temperatures. This permits the gene to be switched off when culturing the bacteria and to be switched on just before the cells are harvested. A DNA sequence coding for such a temperature-sensitive repressor may be introduced into the recombinant vector of the invention by conventional methods.

The invention will now, by way of illustration only, be described in more detail in the following non-limiting examples, reference being made to the accompanying drawings. The disclosures of all the patent and literature references mentioned hereinafter are incorporated by reference herein.

In the drawings:

FIG. 1 is a schematic illustration of a circular restriction map of a plasmid DNA (pSPA1) coding for protein A. The size of the map is given in kilobases starting at the Eco RI restriction site at 12 o'clock, which is a restriction site within the vector pBR322. The positions of the Eco RI, Eco RV, Hind III, Pst I and Bam HI restriction sites are indicated. The junctions between the vector and the inserted DNA are indicated with arrows.

FIG. 2A is a schematic illustration of the protein A coding gene indicating its different regions. Heavy line represents the DNA of the vector pBR322. S is a signal sequence, A-D are IgG-binding regions previously identified, E is a region nearly homologous to A-D, and X is the C-terminal part of protein A which lacks IgG-binding activity.

FIG. 2B is a detailed restriction map of the DNA-sequence corresponding to FIG. 2A, and showing the restriction sites for Taq I, Hind III, Eco RV, Pst I, Bcl I and Sau 3A. The size is given in kilobases starting at the same Eco RI restriction site as indicated in FIG. 1. The junction between the vector pBR322 and the inserted DNA fragment is indicated with an arrow. The restriction sites for Taq I (two) and Sau 3A (one) within the vector sequences have been omitted.

FIGS. 3A-D show the base sequence for the structural protein A gene. Two possible promoters (−35 and −10) and a possible Shine-Dalgarno sequence (indicated by "=") are indicated. The amino acid sequence as deduced from the DNA sequence is also known (the IUPAC amino acid abbreviations are used; J. Biol. Chem. 241, 527 and 249 (1966)). The five amino acids (residues 99, 101 120, 199 and 273) that differ compared to the amino acid sequence reported by Sjödahl supra are indicated as well as the 3 residues (out of 50) in the region E which differ from the corresponding amino acid of region D. The start residues of regions S, E, D, A, B, C and X are indicated by arrows.

FIG. 4 is an autoradiograph of a nucleotide sequence gel showing the junction between regions D and E of FIG. 3. The sequencing (according to Maxam et al, P.N.A.S. 74, 560–564 (1977)) was performed on a DNA fragment labelled at the Bcl I site at position 0,9 kb in FIG. 2. The partially chemically degraded products were resolved in an 8% polyacrylamide sequencing gel (Maizel et al, Methods in Vir. 5, 179–246 (1970)).

FIG. 5 shows SDS5-polyacrylamide gel electrophoresis of IgG-Sepharose ® purified cell extracts. pBR322 and pSPA1 represent extracts of *E. coli* cells carrying the respective plasmid. SPA is commercially available protein A from *S. aureus* (Pharmacia, Uppsala, Sweden). Adeno 2 (AD 2) proteins were used as size markers.

FIG. 6 is a schematic map illustration of plasmid pSPA15, AMP and CML representing genes coding for ampicillin and chloramphenicol resistance, respectively, Ori being replication origins and SPA designating the structural protein A gene.

FIG. 7 is a schematic illustration of the constructions of plasmids containing the whole or parts of the protein A gene. A few restriction sites are shown. Boxes represent structural genes and the arrows indicate the orientation (from start codon towards stop codon). The replication origin is also indicated by Ori. AMP and TET are the genes coding for ampicillin and tetracycline resistance, respectively. PROT A is the gene coding for protein A and lac Z is the gene coding for the N-terminal part of β-galactosidase. (Rüther et al, Nucl. Acids Res. 9, 4087–4098 (1981)).

FIG. 8 is a schematic illustration of the construction of plasmid pSPA16. The abbreviations used are the same as in FIG. 6. S, E, D and B are as in FIG. 2 and A' and C' represent parts of the respective IgG-binding regions A and C of the protein A coding gene.

FIG. 9 is a presentation of the nucleotide sequence, and the corresponding deduced amino acid sequence, around the 3'-end of the protein A gene in plasmid pSPA16.xxx represents the new stop codon.

FIG. 10A-C is a combined illustration, similar to FIG. 2, of the plasmids pSPA15 (B) and pSPA16 (C) together with a corresponding restriction map (A) aligned therewith. Heavy line represents the protein A structural gene.

FIG. 11 is a schematic illustration of the sequencing strategy (C) used for sequencing the 1.8 kb Taq I-EcoRV DNA fragment (B), containing the protein A coding gene (A), to obtain the sequence shown in FIG. 3.

FIG. 12 shows the base sequence around the Sau 3A restriction site at position 1,8 kb in FIG. 2B and around the Pst restriction site at position 2,1 kb. The amino acid sequence as deduced from the DNA sequence is also shown (the IUPAC amino acid abbreviations are used, J.. Biol. Chem. 24, 527 and 2491 (1966).

FIGS. 13A and 13B are schematic illustrations of two fusion vector plasmids. The abbreviations are the same as in FIG. 7. An M13 multilinker has been inserted in the gene coding for protein A at different positions in the two plasmids. The nucleotide sequence and the deduced amino acid sequence of these regions are also shown above the respective plasmid map. FIG. 13A illustrates plasmid pSPA11 and FIG. 13B illustrates plasmid pSPA12.

FIG. 14A and 14B are schematic illustrations of two plasmids containing the genes coding for protein A and β-galactosidase fused together. The abbreviations are the same as in FIG. 7. LAC Z represents the whole gene coding for β-galactosidase except a few nucleotides in the 5'-end thereof. FIG. 14A illustrates plasmid pSPA13 and FIG. 14B illustrates plasmid pSPA14.

FIG. 15 (A, B, C and D) is a schematic illustration of the fused protein A and β-galactosidase genes of the plasmids in FIG. 14A and 14B. In the FIG. A and B are schematic drawings of the protein A gene corresponding to the restriction map of FIG. 2A and 2B, respectively, and in alignment therewith. The sizes are given in base pairs starting at the Taq I site. (The two Bcl sites at nucleotides 355 and 1572 as also Sau 3A sites).

FIG. 16A is a presentation of the nucleotide sequence around the fusion point of plasmid pSPA13 (FIG. 14A). The restriction sites and the corresponding deduced amino acid sequence are indicated. The origins of the different parts of the sequence are also indicated, and FIG. 16B is a corresponding presentation of the nucleotide sequence around the fusion points of plasmid pSPA14 (FIG. 14B).

FIG. 17 shows the nucleotide sequence of a synthetized oligonucleotide and the corresponding phage mp9/IGF-1 sequence at the point of mutagenesis. "*" indicates a non-complementary base pair. The decuded amino acid sequence after mutagenesis is also shown.

FIG. 18 is a schematic illustration of the construction of shuttle vectors containing the IGF-1 and the protein A genes. A few restriction sites are shown. Boxes represent structural genes and the arrows indicate the orientation (from start codon towards stop codon). The replication origins are also indicated by ORI-E (*E. coli*) and ORI-S (*S. aureus*). AMP, TET and CML are the genes for ampicillin, tetracycline and chloramphenicol resistance, respectively. PROT A is the gene coding for protein A and IGF-1 is the gene coding for the modified human insulin-like growth factor, type 1.

FIG. 19 is a presentation of the nucleotide and the deduced amino acid sequence of the gene fusion between protein A and IGF-1 in plasmid pUN201. Only the DNA-sequence coding for the mature protein A (lacking the region coding for the signal peptide) is shown. Possible amino acid cleavage points with formic acid treatment (Asp-Pro) are underlined. Cleavage sites for Eco RI and Hind III are shown, said cleavage sites representing the end points of a synthetic modified IFG-1 gene.

FIG. 21A is a presentation of two DNA-strands representing the IGF-1 gene and flanking sequences, divided into oligomers. The sequence has been provided with a start codon (ATG in block A2), a stop codon (TAG in block A17) and recognition sequences for Eco RI (block A1) and Hind III (block A17).

Figure 1:
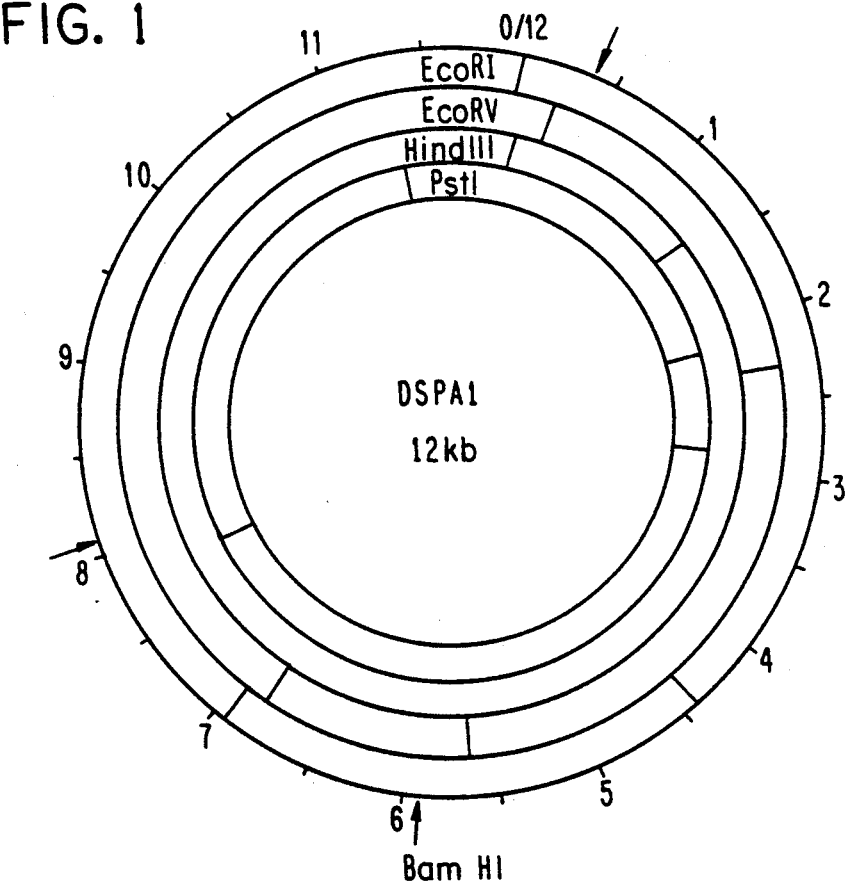

RECOMBINANT DNA MOLECULE, TRANSFORMED MICROORGANISM AND PROCESS FOR PRODUCING PROTEIN A AS DESCRIBED IN THE INTERNATIONAL PATENT APPLICATION PCT/SE83/00297 (SWEDISH PATENT APPLICATION 8204810-9)

In the Examples the starting materials, buffers, cell media and routine method steps were as follows.

STARTING MATERIALS

Bacterial hosts Four strains of *E. coli* K12 were used in the Examples: HB101, described by Boyer et al, J. Mol. Biol. 41, 459–472 (1969); 259, described by Jacob, F. and Wollman, E. C. Ann. Inst. Pasteur 91, 486–510 (1956); GM161, described by Marinus, M. G., Molec. gen. Genet. 127, 47–55 (1973); RRI del M15 (Langey et al, Proc. Natl. Acad. Sci., USA, 72, 1254–1257 (1975)). (the strains are available at the Department of Microbiology (N), Biomedical Centre, Uppsala, Sweden).

Also, the following four Staphylococcus strains were used:

*S. epidermidis* 247, described by Rosendorf et al, J. Bacteriol. 120: 679–686 (1974); obtained from Inst. of Medical Microbiology, Univ. of Zürich, Switzerland;

*S. xylosus* KL117, described by Schleifer et al, Int. J. Syst. Bacteriol. 25: 50–61 (1975) and Schleifer et al, Arch. Microbiol. 122: 93–101 (1979); obtained from Inst. for Microbiology, Technical Univ. of Munich, Federal Republic of Germany;

*S. aureus* SA113, described by Iordanescu et al (J. Gen. Microbiol. 96: 277–281 (1976));

*S. aureus* 320, a protein A negative mutant of strain *S. aureus* 113 isolated at the Department of Microbiology, Biomedical Centre, Uppsala, Sweden and described by Jonsson et al, Curr. Microbiol. 8: . . . (1983).

Cloning vehicles. The cloning vehicles used in the Examples were pBR322 as constructed and described by Bolivar et al, Gene 2, 95–113 (1977); pBR328 as constructed and described by Soberon, X., et al, Gene 9, 287–305 (1980); pTR262 as constructed and described by Roberts, T. M., et al, Gene 12, 123–127 (1980); pHV14 as constructed and described by Ehrlich, S. D., Proc. Natl. Acad. Sci. USA 70, 3240–3244 (1978), and pHV33 as constructed and described by Primrose, S. B. and Ehrlich, S. D., Plasmid 6, 193–201 (1981). pUR222 as constructed and described by Rüther et al, Nucl. Acids Res., 9, 4087–4098 (1981);

BUFFERS AND MEDIA

Triton-mix: 0.1% Triton X-100, 0.125M EDTA and 20 mM Tris (pH 8.0).

Tris-EDTA buffer ("TE"): 0.001M EDTA and 0.01M Tris (pH 7.8).

CY broth: Difco casein hydrolysate 1%, Difco yeast extract 1% and glucose 0.5%; 4 ml of 1.5M glycerolphosphate is added to 100 ml of CY broth.

Coating buffer (carbonate-bicarbonate-pH 9.6): 1.59 g $Na_2CO_3$, 2.93 g $NaHCO_3$ and 0.2 g $NaN_3$, made up to 1 liter with distilled $H_2O$.

PBS TWEEN (Phosphate buffered saline plus 0.05% TWEEN ®): 8.0 g NaCl, 0.2 g $KH_2PO_4$, 2.9 g $Na_2HPO_4 \times 12 H_2O$, 0.2 g KCl, 0.5 ml TWEEN ® 20 and 0.2 g $NaN_3$, made up to 1 liter with distilled $H_2O$; pH 7.4.

Diethanolamine buffer 10%: 97 ml diethanolamine, 800 ml distilled $H_2O$, 0.2 g $NaN_3$, and 100 mg $MgCl_2 \times 6 H_2O$; pH adjusted to 9.8 with 1M HCl; made up to 1 liter with distilled $H_2O$.

Luria-broth ("LB"): 10 g Difco tryptone, 5 g Difco yeast extract, 0.5 g NaCl, 2 ml 1M NaOH; adjusted to pH 7.0 with 1M NaOH; 10 ml 20% glucose added after autoclaving.

LA-medium: Luria-broth supplemented with 1% Difco agar.

TEB buffer: 0.09M Tris-borate, 0.09M boric acid and 0.002M EDTA.

ROUTINE METHODS

Certain procedures were carried out repeatedly in the Examples. Unless otherwise specified, they were done exactly as follows each time that they were carried out.

Transformations. Transformation of *E. coli* K12, with plasmid DNA, was performed exactly as described by Morrison, D. A., Methods in Enzymology, Academic Press 68, 326-331 (1979). The transformed cells were selected in a conventional manner on plates by plating for single colonies on LA plates containing suitable antibiotics, i.e. 35 μg/ml of ampicillin or 25 μg/ml of chloroamphenicol.

Isolating plasmids. Large scale plasmid preparation was performed exactly as described by Tanaka, T. and Weisblum, B., J. Bacteriol. 121, 354-362 (1975). For scoring a large number of clones for plasmids the "mini alkali method" was used exactly as described by Birnboim, H. C. and Doly, J., Nucl. Acids Res. 7, 1513-1523 (1979).

Restriction enzyme digestion of DNA. DNA was cleaved with conventional restriction enzymes purchased from New England Bio Labs, Waltham, Mass., USA. The restriction enzymes were added to DNA at conventional concentrations and temperatures and with buffers as recommended by New Englad Bio Labs.

Ligating DNA fragments. All DNA fragments were ligated at 14° C. over-night with T4 DNA ligase purchased from New England Bio Labs, Waltham, Mass., USA, in a buffer recommended by the supplier.

Agarose gel electrophoresis. 0.7% agarose gel electrophoresis for separating cut plasmid fragments, supercoiled plasmids, and DNA fragments 1000 to 10,000 nucleotides in length was performed exactly as described by Helling et al, J. Vir. 14, 1235-1244 (1974).

Polyacrylamide gel electrophoresis. 5% polyacrylamide gel electrophoresis for the separation of DNA fragments 100 to 4000 nucleotides in length was performed exactly as described by Maxam et al, P.N.A.S. 74, 560-564 (1977). 13% polyacrylamide gel electrophoresis for the separation of proteins of molecular weights of 5,000 to 120,000 was performed exactly as described by Maizel et al, Methods in Vir. 5, 179-246 (1970).

Gel elution. DNA fragments were eluted from either polyacrylamide or agarose gel pieces exactly as described by Maxam et al, P.N.A.S. 74, 560-564 (1977).

DNA sequencing. DNA fragments were 5' end labeled, and their DNA sequences were determined exactly as described by Maxam et al, supra. The 5' end of endonuclease generated DNA fragments was labelled with ($\gamma$-$^{32}$P) ATP (New England Nuclear, USA; 2700 Ci/mmol) using T4 polynucleotide kinase (Boehringer, Mannheim, West Germany).

Preparation of cell lysate for detection of protein A. *E. coli* clones were grown overnight at 37° C. in 50 ml Luria-broth (LB) with ampicillin added at 35 μg/ml. After centrifugation the cells were resuspended in 5 ml Tris-EDTA (0.05M, pH 8.5, 0.05M) and centrifuged. The cells were resuspended in 5 ml of the same buffer and lysozyme was added to a final concentration of 2 mg/ml. After 1 hour at 37° C. the lysate was centrifuged in a Sorvall SS-34 rotor at 15,000 rpm for 15 minutes. The supernatant was collected and assayed for protein A.

Detection and quantification of protein A from *E. coli* clones. An ELISA-test (enzyme linked immunosorbent assay) was used for detection and quantification of produced protein A. The test makes use of a special microtiter plate (Titertek, Amstelstad, the Netherlands) having no net charge (neutral), the wells of which are coated with human IgG (Kabi, Sweden). Test samples are then added to allow protein A to bind to the Fc-part of the IgG-molecules. The amount of remaining free Fc-sites is then titrated by adding alkaline phosphatase linked to protein A. After washing of the wells, p-nitrophenyl-phosphate is added as a substrate for alkaline phosphatase.

Assay: The wells of a microtiter plate were filled with 50 μl of a solution of human IgG (Kabi, Sweden) at 500 μg/ml in a coating buffer and the plate was incubated at room temperature for 1 hour. The wells were then washed three times with PBS+0.05% Tween® 20, which was used in all washes in the assay, and 50 μl of the lysate to be tested was added. For quantitative determinations twofold serial dilutions of the lysates in PBS+0.05% Tween® 20 were made. 10 μl of PBS+0.1% Tween® 20 was then added and incubation was allowed for 1 hour at room temperature. The wells were again washed three times, and 50 μl of protein A-alkaline phosphatase conjugate (prepared exactly as described in Immunochemistry, Pergamon Press 1969, Vol. 6 pp. 43-52) was added. After 1 hour of incubation at room temperature the wells were again washed three times and 100 μl of alkaline phosphatase substrate (Sigma 104=p-nitrophenyl-phosphate at 1 mg/ml) was added. The enzyme reaction was interrupted after 30 minutes by the addition of 10 μl of 3M NaOH. The result was determined visually. A positive result, i.e. presence of protein A, is a colour-less reaction mixture, since no free Fc-sites of IgG are available to bind the conjugate. A negative result, i.e. no protein A, is observed as a yellow colour due to the activity of the alkaline phosphatase of the bound conjugate. Quantitative determinations of protein A were made by running serial twofold dilutions of a protein A standard solution of known concentration in parallel with the test samples.

EXAMPLE I

Cloning of protein A in *E. coli*

A. Preparation of staphylococcal chromosomal donor DNA. *S. aureus* strain 8325-4 (∅11) mec-4916, str-4916, nov-142 (described by Sjöström, J.-E., et al, J. Bacteriol. 123, 905-915 (1975) and available from the Department of Microbiology (N), Biomedical Center, Uppsala, Sweden) was grown to OD$_{540}$=0.2 in Cy broth. One liter of cell culture was harvested by centrifugation at 5,000 rpm in a Sorvall GSA rotor, resuspended in 100 ml of 0.9% NaCl and 10 mM Tris, pH 7.2, and centrifuged at 5,000 rpm in a Sorvall GSA rotor. The cell pellet was finally resuspended in 10 ml of 25% sucrose, 50 mM Tris pH 7.2 and protoplasts were prepared by lysostaphine treatment (15 μg/ml) at 37° C. for 30 min. The protoplasts were lysed by addition of 10 ml of Triton-mix and 5 ml of H$_2$O. The mixture was left on ice and occasionally gently shaken until complete lysis. The DNA was treated with proteinase K (0.1 mg/ml) and SDS (sodiumdodecyl sulfate) (0.5%) for 1 hr at 37° C. followed by five phenol extractions with equal volumes of phenol, and finally two chloroform extractions. Sodium acetate, pH 7.0, was added to 0.3M, and the DNA was precipitated with two volumes of cold ethanol. The precipitate was washed stepwise in 70, 80, 90 and 99% cold ethanol. The precipitate was dissolved in TE buffer by gentle mixing at 37° C. Finally the DNA was dialysed against TE buffer.

B. Partial digestion of chromosomal DNA and isolation of donor fragments. Purified staphylococcal DNA from step A was digested with various concentrations of the restriction enzyme Mbo I. Each reaction was made in 50 μl volume with 1 μg of DNA and the reaction was stopped by heat inactivation at 65° C. for 10 min. The extent of digestion was determined by agarose gel electrophoresis. The concentration of Mbo I giving a large partial cleavage product of 5 to 20 kilobases was chosen for a preparative digest of 100 μg of staphylococcal DNA in 5 ml. This digest was heat inactivated, precipitated with ethanol, dissolved in 100 μl of TE and sedimented through a 10–30% sucrose gradient in TE buffer. A Beckman Sw40 rotor was used at 5° C., 35 rpm, for 20 hrs. The gradient was fractioned into 0.5 ml fractions, each of which was analyzed by agarose gel electrophoresis. The fractions with 8–10 kb fragments were pooled, precipitated with 2 volumes of ethanol and dissolved in TE buffer.

C. Digestion and alkaline phosphatase treatment of the vector pBR322. One μg of pBR322 was digested with Bam Hl for 2 hrs at 37° C., and the enzyme was inactivated at 65° C. for 10 minutes. The DNA was treated with alkaline phosphatase in order to remove the 5' phosphate. This treatment eliminated the possibility to re-ligate the vector. The reaction was effected in 50 mM Tris, pH 7.9, 5% DMSO and 1 unit of calf intestinal alkaline phosphatase at 37° C. for 30 minutes in 1 ml. 0.5% SDS was added and the DNA was phenol extracted twice. Traces of phenol were removed by ether and the DNA was precipitated by two volumes of ethanol.

D. Insertion of staphylococcal DNA into pBR322, transformation of *E. coli* and negative selection for recombinants. The vector pBR322 chosen for the original cloning of staphylococcal DNA codes for tetracycline (tet) and ampicillin (amp) resistance. When pBR322 is opened up by digestion with Bam Hl, as in step C above, and a DNA fragment is inserted, the gene for tetracycline resistance is inactivated. By testing transformants for sensitivity to tetracycline recombinants can be found—so-called negative selection. 0.5 μg of pBR322 treated according to Step C and 2 μg of staphylococcal DNA treated according to Step B were mixed and ligated in a total volume of 25 μl overnight at 14° C. The mixture was used to transform *E. coli* 259 with selection for ampicillin resistance (35 μg/ml). Transformants were picked and streaked on plates containing 10 μg/ml of tetracycline and plates containing 35 μg/ml of ampicillin, respectively. Transformants that grew on ampicillin but not on tetracycline were considered as recombinants.

E. Detection of protein A positive *E. coli* clones. Five hundred tetracycline sensitive clones from Step D were grown as separate colonies on LA-plates (prepared from LA-medium) containing ampicillin (35 μg/ml). Groups of 25 colonies were collected and inoculated into 50 ml of LB-broth with 35 μg of ampicillin and grown overnight. Cell extracts were prepared by lysozyme+EDTA treatment (as described under Routine Methods) and tested for protein A by the ELISA-test described under Routine Methods. One of these groups of clones was positive, and this positive group was further subdivided into 5 groups of 5 clones each and grown and treated as above. Finally in a last series of tests one protein A producing clone, *E. coli* SPA 11 containing the plasmid pSPA1, was found. Cultures of this clone have been deposited with the collection of the Deutsche Sammlung von Mikroorganismen (DSM), Grisebachstrasse 8, 3400 Göttingen, Federal Republic of Germany, on July 12, 1982 where it was assigned No. DSM 2434.

F. Restriction map of pSPA1. In order to get information for subcloning and sequencing the gene coding for protein A, a restriction map of pSPA1 obtained in Step E was made. This was done with single, double and/or triple digests with the enzymes indicated in FIGS. 1 and 2. FIG. 2 shows a more detailed map in the area coding for protein A. Summing up the sizes of the various restriction fragments gives a total size of 12 kb for pSPA1, and thus the donated staphylococcal fragment amounts to approximately 7.6 kb.

G. Subcloning of the protein A coding gene from pSPA1 into plasmids pBR328 and pHV14. In order to locate the position of the gene several subclones were constructed and tested for protein A activity. 2 μg of plasmid pSPA1 from Step E and 1 μg of pBR328 were cut with the restriction enzyme Eco RV, mixed, treated with T4-ligase and used to transform *E. coli* HB101. Cleavage, ligation and transformation were realized as described above under Routine Methods. Colonies containing recombinants were selected as being chloramphenicol resistant and tetracycline sensitive in analogous manner as described in Step D. 8 colonies out of 48 of these recombinants were discovered to be protein A positive using the ELISA method described under Routine Methods. Restriction analysis, according to Step F, showed that all 8 clones contained pBR328 having a 2.15 kb Eco RV insert derived from the fragment corresponding to 0.2 kb to 2.35 kb of the pSPA1 restriction map of FIG. 1. All clones had the insert in the same orientation giving a functional tet promoter reading with the inserted gene.

One clone containing this plasmid, designated pSPA3, was selected for further studies. In order to determine whether the protein A gene could be transcribed from a promoter of its own, the plasmid pSPA3 was used as a source to reclone it into the plasmid pHV14. This plasmid, which is derived from pBR322, has a 2.8 kb insert in the Hind III restriction site, thus inactivating the tet-promoter. Any insert in the Eco RV restriction site of this plasmid therefore must have a functional promoter of its own in order to be transcribed by *E. coli* RNA polymerase. 1 μg of pSPA3 and 1 μg of pHV14 were cut with Eco RV, admixed, treated with T4-ligase and used to transform *E. coli* HB101. Cleavage, ligation and transformation were effected as described above. Colonies were selected as being ampicillin resistant and tetracycline sensitive as described in Step D.

Plasmids from 52 of these colonies were isolated by the "mini alkali method" referred to under Routine Methods and tested by running on 0.7% agarose gel electrophoresis. One of these clones was discovered to be a recombinant of pHV14 having the above mentioned 2.15 kb Eco RV insert from pSPA3. The clone containing this plasmid, designated pSPA5, was found to be protein A positive when tested using the ELISA method. It was concluded that the insert must contain a staphylococcal promoter reading into the protein A gene which also is functional in *E. coli* HB101.

Figure 2A:
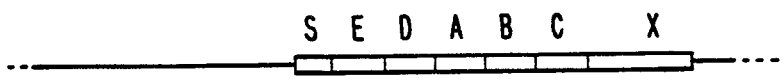
Figure 2B:
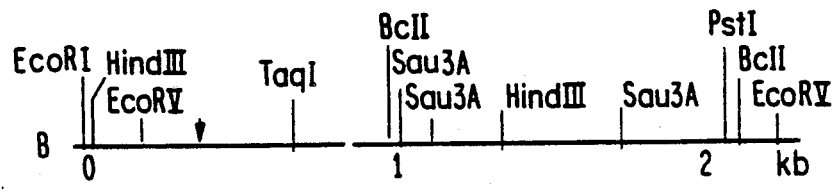
Figure 3A:
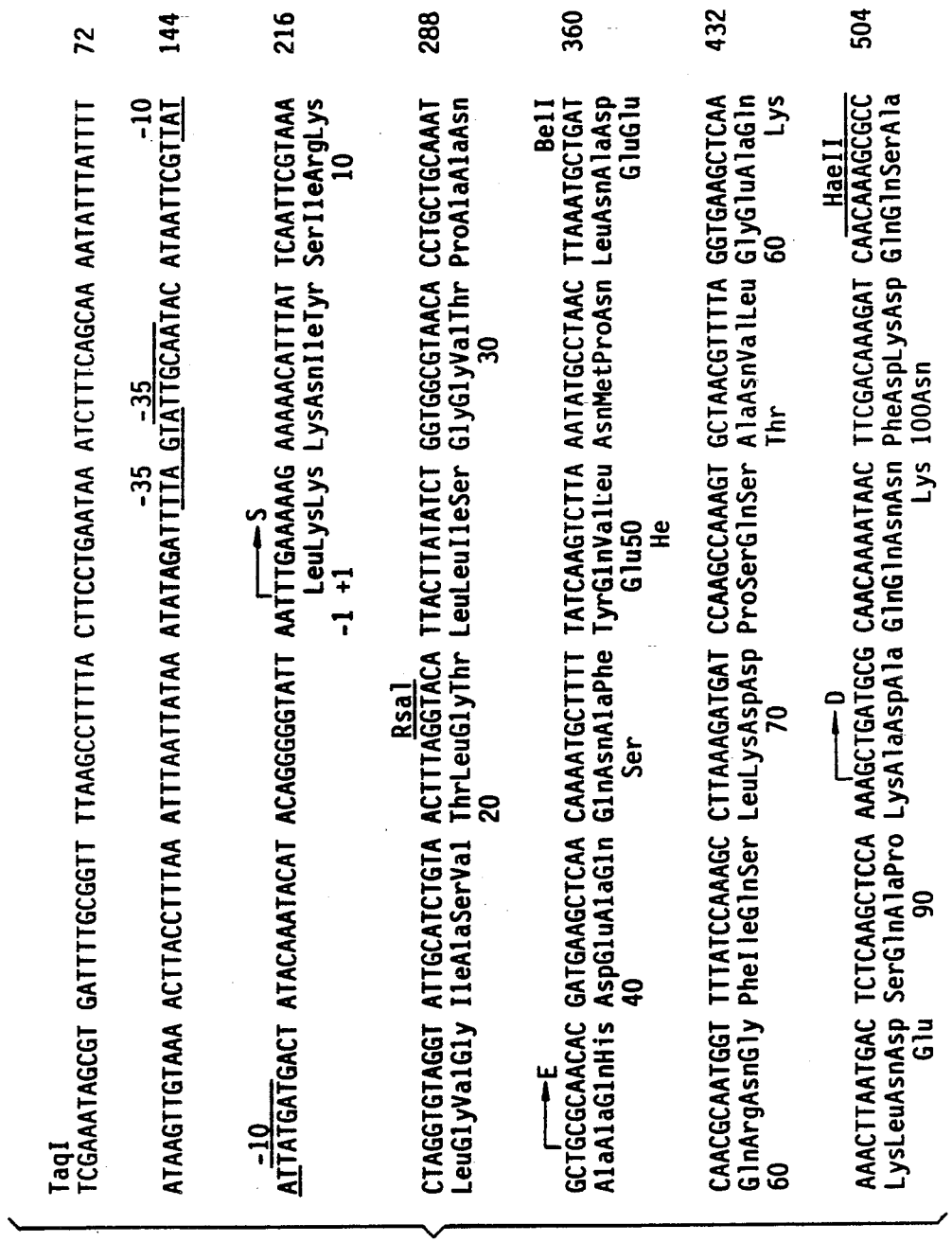
Figure 4:
Figure 11A:
Figure 11B:
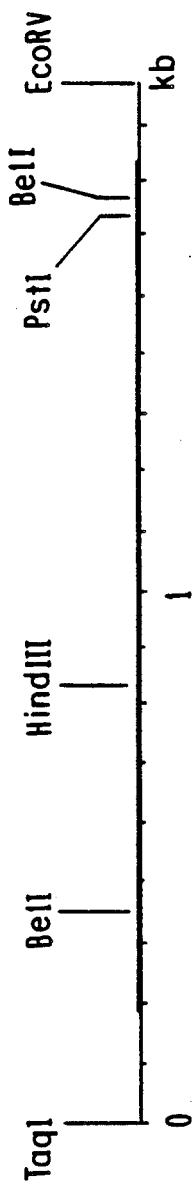
Figure 11C:
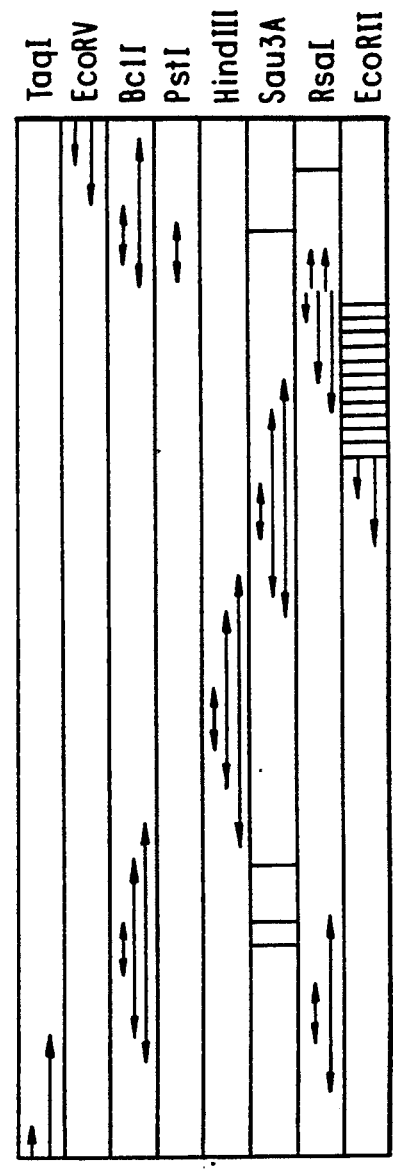
Figure 15A:
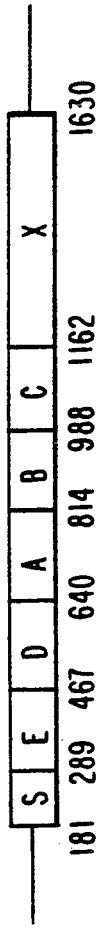
Figure 15B:
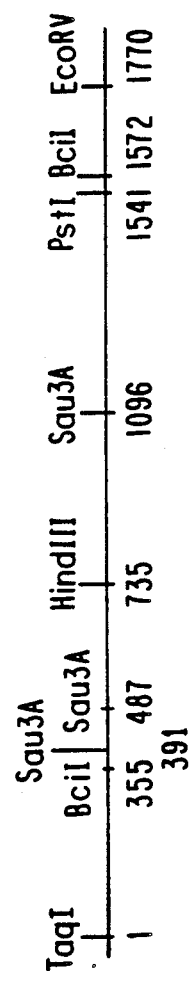
Figure 15C:
Figure 15D:

Analysis of the DNA sequence of the protein A gene. The results of the subcloning indicated that DNA-sequencing should be started at the Hind III-site at map position 1.4 kb going counter-clockwise (FIG. 1). The DNA source for the sequencing analysis was purified pSPA3. By comparing the partially known amino acid sequence of protein A (as reported by Sjödahl supra) with the obtained DNA sequence the position of the HIND III-site in the gene could be located. As shown in FIGS. 2 and 3 this restriction site is within region A of protein A. By further analysis, according to Step F, restriction sites for the enzymes Taq1, Rsa I, Bcl I, Sau 3A and Pst I were determined (FIG. 2). These sites were used for sequencing in one or both directions giving in most cases nucleotide sequences of both strands. The strategy used for the sequencing is outlined in FIG. 11. As Bcl I does not cleave DNA purified from *E. coli* HB101, pSPA3 was transformed into the strain *E. coli* GM 161 lacking the enzyme D-alanine methylase. pSPA3 repurified from this strain was cleaved with Bcl I for sequencing.

FIG. 3 shows the DNA sequence of the whole staphylococcal protein A gene. The amino acid sequence deduced from the DNA sequences is also indicated together with the differing amino acids as compared to the sequence proposed by Sjödahl supra, which was made on another strain of *S. aureus* (Cowan I).

The DNA sequence illustrated in FIG. 3 reveals an N-terminal region called E similar to the repetitive regions D-A-B-C reported by Sjödahl supra. This region of 50 amino acids has 42 amino acids which are identical to region D.

Region E is preceded by a leader sequence with the characteristics of a signal peptide containing a basic region of 11 amino acids followed by a hydrophobic stretch of 23 amino acids. The exact cleavage site is not known, but possible sites are at alanine residues 36, 37 or 42, probably at 36. If so, the amino acid sequence 37-42 belongs to region E of the protein A molecule. The initiation codon for translation is TTG similar to a few other reported initiation codons from gram-positive bacteria. Six nucleotides upstream TTG a Shine-Dalgarno sequence (defined in Shine, J. and Dalgarno, L. Nature (London) 254, 34-38 (1975)) is found which has many features in common with other grampositive ribosome binding sites. Further upstream two possible promoters are found at $-35$ and $-10$ (FIG. 3).

By calculating the number of bases necessary to code for the whole protein it seems that both pSPA1 and pSPA3 contains the complete protein A structural gene.

Analysis of the gene product from *E. coli* containing pSPA1. *E. coli* cells carrying pSPA1 were grown overnight in 400 ml of LB with ampicillin, 35 μg/ml, added. The cell culture was centrifuged at 6000 rpm with a Sorvall GSA-rotor for 10 min. and the cell pellet was washed in 20 ml of TE (0.05M, pH 8.5, 0.05M EDTA) and again centrifuged as above. This time the cell pellet was resuspended in 15 ml of a protease inhibitor buffer (0.02M potassium phosphate, pH 7.5, 0.1M NaCl, 0.5% sodium deoxycholate, 1% Triton X-100, 0.1% sodium-dodecyl sulfate (SDS), and 1 mM phenylmethylsulfonyl fluoride (PMSF)). The cells were then sonicated in a MSE sonicator for 4×40 sec. on an ice-bath and centrifuged at 15,000 rpm (Sorvall SS-34 rotor) for 10 min. The supernatant was collected and passed over an IgG-Sepharose ® 4B column (Pharmacia, Uppsala, Sweden) (Hjelm et al, FEBS Lett. 28, 73-76 (1972)) that had been equilibrated with a sodium acetate buffer (0.1M sodium acetate, 2% NaCl, pH 5.5). The column was then washed with the same buffer as above and the adsorbed protein A eluted with a glycine buffer (0.1M glycine, 2% NaCl, pH 3.0). To the eluted fractions 1/9 volume of 100% trichloroacetic acid (TCA) was added.

The samples were precipitated for 6 hours at $+4°$ C. and centrifuged at 12,000 rpm in an Eppendorf centrifuge for 15 min. The pellets were washed once in 1 ml of cold acetone and then centrifuged as above. The remaining pellets were dried, dissolved in TE and pooled to give a total volume of 400 μl.

Figure 5:
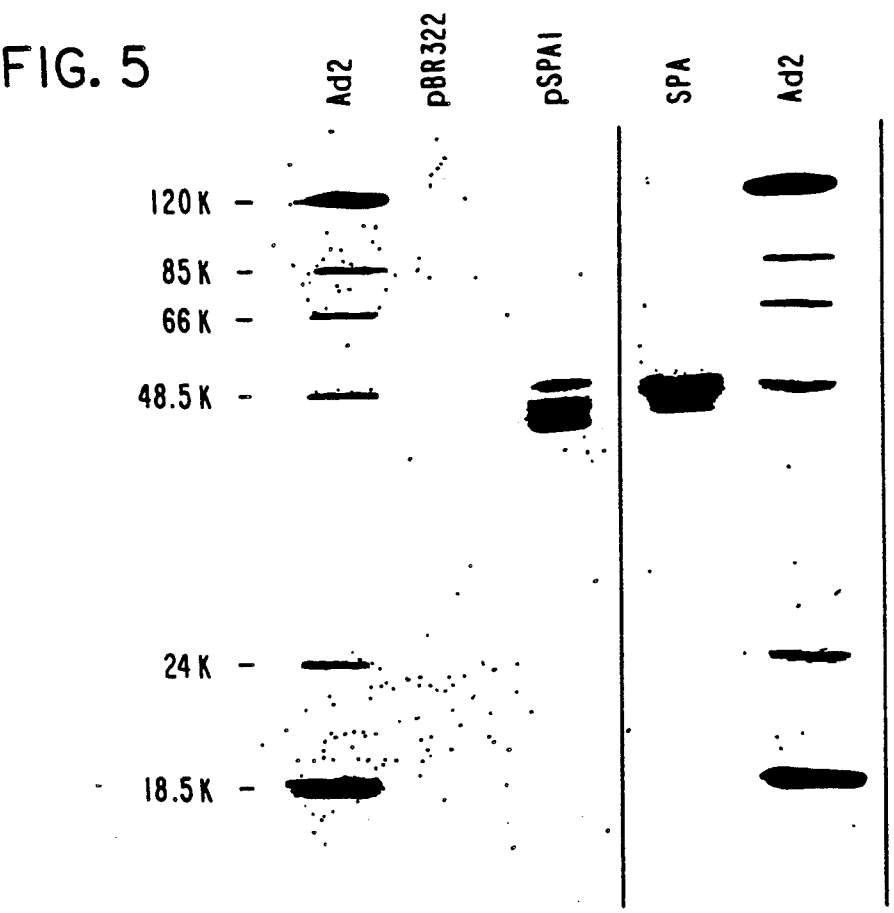

The protein concentration was determined, and 20 μg were analyzed on a 13% SDS-polyacrylamide gel at 100 V for 12 hrs. The gel was stained with amidoblack (0.1%, 45% methanol, 10% acetic acid). An extract from cells carrying pBR322 was prepared in parallel and the same volume as above was analyzed on the gel. The results of the gel electrophoresis are shown in FIG. 5 indicating that protein A produced in *E. coli* carrying pSPA1 migrated close to pure protein A from *S. aureus* (from Pharmacia, Uppsala, Sweden). The extract from cells carrying the pBR322 plasmid had no corresponding protein.

Analysis of localization of protein A in *E. coli*. Enzymes, which in gram-positive bacteria are extracellular, are in gram-negative bacteria often located between the inner and outer membranes in the so-called periplasm or periplasmic space. Since protein A is located in the cell wall and thus outside the cell membrane in *S. aureus*, the localization of the protein in the transformed *E. coli* cells containing pSPA1 was determined. For this purpose the osmotic shock procedure as described by Heppel, L. A., Science 158; 1451-1455 (1967) was used. This procedure releases proteins from the periplasmic space but not intracellular enzymes. Alkaline phosphatase was used as an example of a protein found in the periplasmic space and phenylalanine-tRNA synthetase as an example of an intracellular protein.

*E. coli* containing pSPA1 was grown in a low phosphate medium (exactly as described by Neu, H. g. and Heppel, L. A., J. Biol. Chem. 240; 3685-3692 (1965)) to derepress the synthesis of alkaline phosphatase. One liter of an overnight culture (approximately $7.5 \times 10^8$ CFU/ml) was divided into two portions. One portion was washed three times in cold 0.01M Tris-HCl buffer, pH 8.1, and the cells resuspended in 20 ml of 20% sucrose-0.03M Tris-HCl, pH 8.1, 1 mM EDTA. After 10 min. on a rotary shaker at room temperature the mixture was centrifuged for 10 min. at 13,000×g in a Sorvall centrifuge. The supernatant was removed and the well drained pellet was rapidly mixed with 20 ml of cold $5 \times 10^{-4}$M MgCl$_2$ solution. The suspension was mixed in an icebath on a rotary shaker for 10 min. and centrifuged. The supernatant termed "the osmotic shock wash" was collected for further testing. For comparison the other portion of cells was centrifuged, washed and resuspended in 5 ml of polymix-buffer (I) (exactly as described by Jelenc, P. C., Anal. Biochem. 105; 369-374 (1980)). The cells were disintegrated in an X-press as recommended by the manufacturer (Biotec, Stockholm, Sweden). The cell debris were removed by centrifugation at 13,000 rpm for 15 min. in a Sorvall SS-34 rotor centrifuge and the supernatant was collected for further testing.

The two extracts obtained containing perisplasmic and whole cell protein, respectively, were each assayed for alkaline phosphatase and phenylalanine-tRNA synthetase with the enzymatic assays indicated below, and for protein A as described above under Routine Methods.

Enzymatic assays. Alkaline phospatase was assayed in a Tris-buffer, 0.05M, pH 8.0, using p-nitrophenyl-phosphate ($4 \times 10^{-4}$M) as substrate (Sigma 104). Hydrolysis of p-nitrophenyl-phosphate was measured in a spectrophotometer at 410 mμ. One unit of activity represented a change in absorbance at 410 mμ of 1.0 per minute. (Heppel, L. A., Harkness, D. R. and Hilmoe, R. J., J. Biol. Chem. 237, 841–846 (1962).

Phenylalanine-tRNA synthetase. The assay was performed in a mixture containing in a total volume of 100 μl; 5 mM Mg(OAc)$_2$, 0.5 mM CaCl$_2$, 95 mM KCl, 5 mM NH$_4$Cl, 8 mM putrescine, 1 mM spermidine, 5 mM K-phosphate, pH 7,5, 1 mM dithioerythritol, 1 mM ATP, 6 mM phosphoenolpyruvate, 1 μg pyruvate kinase (Sigma, St. Louis, USA), 1 unit of myokinase (Sigma), 100 μM ($^{14}$C)-phenylalanine (4 cpm/pmol) (Radiochemical centre, Amersham, England), 300 μg of total E. coli tRNA (Boerhringer/Mannheim, Federal Republic of Germany).

The X-pressed cell extract and the osmotic shock wash were tested by the addition of 10 μl of suitable dilutions. The enzyme assays were run for 15 min. at 37° C. Cold 10% TCA was added to interrupt the reaction and to precipitate phenylalanine-tRNA. The precipitate was collected on glass fibre filters, (GFA, Whatman), washed with 10% cold TCA and cold 70% ethanol and the radioactivity measured. One unit of activity is defined as the formation of 1 pmole of Phe-tRNA per minute. (Wagner, E. G. H., Jelenc, P. C., Ehrenberg, M. and Kurland, C. G., Eur. J. Biochem. 122, 193–197 (1982)).

The results are presented in the following Table 1. All figures in the table are calculated per 500 ml cell culture (approx. $7.5 \times 10^8$ CFU/ml).

TABLE 1

Enzyme activities and protein A content of E. coli cells containing pSPA1

|  | Periplasm of cells | Whole cells |
| --- | --- | --- |
| Alkaline phosphatase (units) | 160 | 210 |
| Phenylalanine-tRNA synthetase (units) | 0 | 1530 |
| Protein A (μg)[a] | 24–48 | 24–48 |

[a]Since the determination is made in serial two-fold dilutions the amounts are presented as lying within the range of two dilution steps.

Table 1 shows that protein A and alkaline phosphatase were released when the cells were subjected to osmotic shock, while no activity of the intracellular enzyme phenylalanine-tRNA synthetase was detected in the osmotic shock wash. This result indicates that the S. aureus signal sequence, which according to the sequence data (FIG. 3) is present in the cloned DNA, is expressed in E. coli, and that the signal peptide is recognized by the membrane. In a gram-positive bacteria, lacking the outer membrane, such as e.g. Bacillus subtilis, the signal peptide would most likely have effected secretion of the protein A into the growth medium.

The amounts of protein A produced by the pSPA1 carrying E. coli cells are about 1–2 mg/liter medium.

EXAMPLE II

Cloning of Protein A in Various Staphylococcal Strains

I. Construction of shuttle vectors containing the protein A gene.

Two shuttle vectors containing the protein A gene were constructed to enable replication both in E. coli, S. aureus and coagulase-negative staphylococci. The plasmid vector pHV33 based on the staphylococcal plasmid pCl94, was used expressing ampicilin and tetracycline resistance in E. coli and chloramphenicol resistance in staphylococci.

Figure 6:
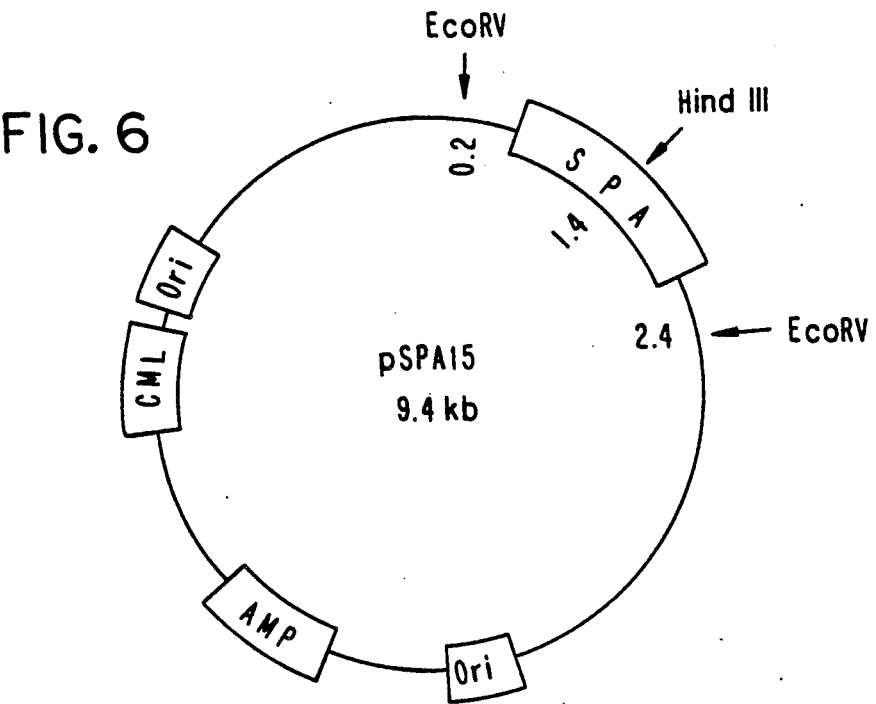

A. Construction of shuttle vector plasmid pSPA15 (FIG. 6).

The first shuttle vector was constructed by cloning the 2,1 kb EcoRV fragment containing the protein A gene as described in Example I, step G, into the EcoRV site of plasmid pHV33. 2 μg of plasmid pSPA3, from step G of Example I, and 1 μg of pHV33 were cut with EcoRV, mixed, treated with T4-ligase and used to transform E. coli HB101. Cleavage, ligation and transformation were performed as described above under Routine Methods. Colonies containing recombinants were selected as being ampicillin resistant and tetracycline and chloramphenicol sensitive in analogous manner as described in step D of Example I. Restriction analysis according to step F of Example I showed that out of 8 tested clones all contained the plasmid shown schematically in FIG. 6. All clones had the insert in the same orientation as in plasmid pSPA3 (see step G, Example I). One clone containing this plasmid, designated pSPA15, was selected for further studies. This plasmid was found to contain the whole structural gene of protein A coding for a mature protein of 447 amino acids and a predicted molecular weight of 49,604.

B. Construction of shuttle vector plasmid pSPA16 (FIG. 8).

Figure 7:
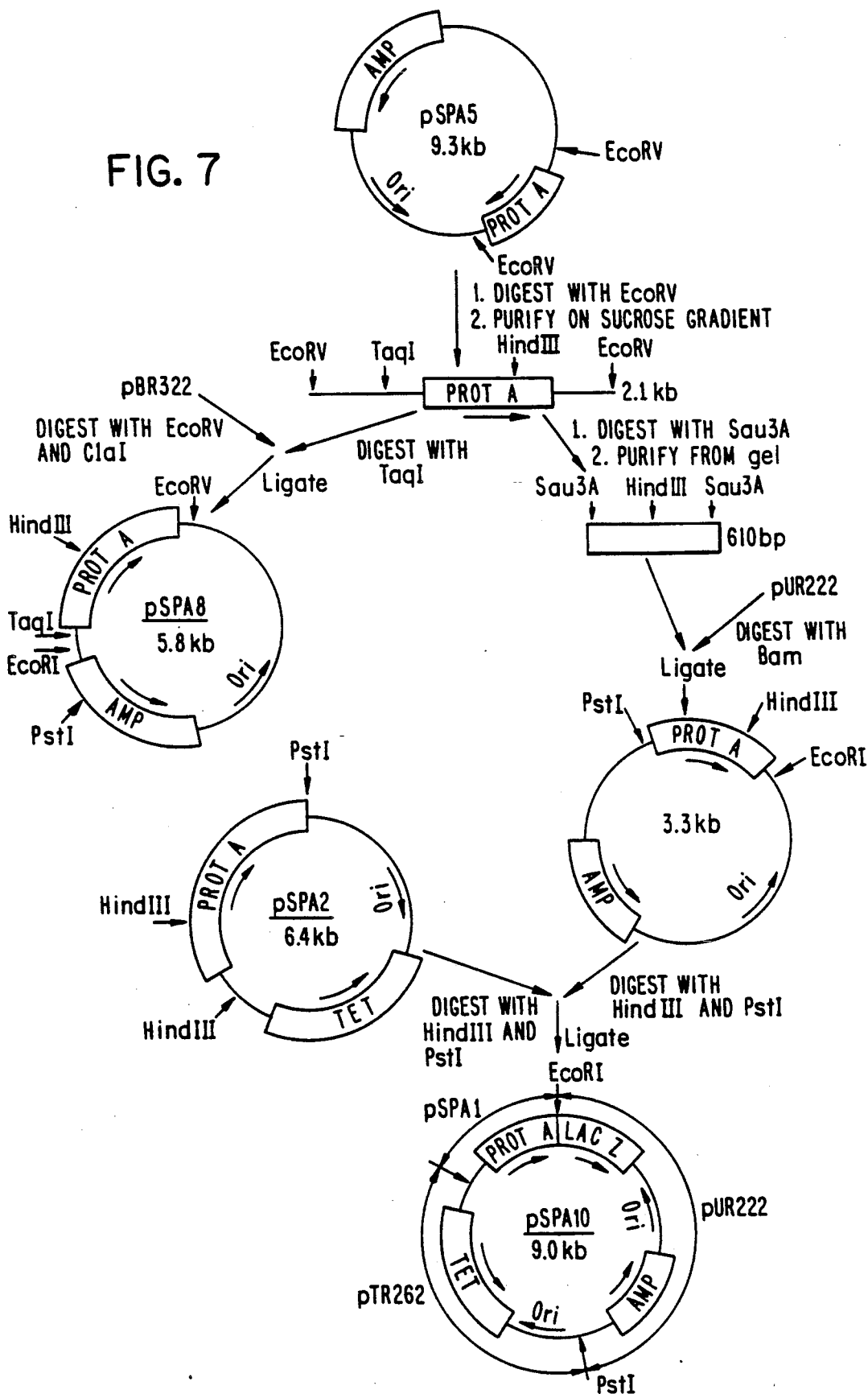

B1. Subcloning of the 5'-end of the protein A gene from pSPA1 into plasmid pTR262 to obtain plasmid pSPA2 (FIG. 7)

1 μg of plasmid pSPA1 (see FIG. 1) from step E of Example I, and 1 μg of plasmid pTR262 were cut with restriction enzymes Hind III and Pst I, mixed, treated with T4-ligase and used to transform E. coli HB101. Cleavage, ligation and transformation were effected as described above under Routine Methods.

Plasmid pTR262 contains a lambda repressor gene which on expression inactivates the gene for tetracycline resistance. The lambda repressor gene has a Hind III site and insertion of a DNA sequence into the latter therefore inactivates the lambda repressor gene and activates the tetracycline resistance gene. Plasmid pTR262 thus permits positive selection for tetracycline resistant recombinants.

Colonies containing recombinants were thus selected as being tetracycline resistant. 1 colony out of 20 of these recombinants was discovered to be protein A positive using the ELISA method described hereinbefore under Routine Methods. Restriction analysis indicated that it contained vector plasmid pTR262 having a 2.1 kb protein A gene insert derived from the fragment corresponding to 0.0 to 2.1 kb of the pSPA1 restriction map of FIG. 1 and 2B. This plasmid was designated pSPA2 and is shown schematically in FIG. 7. It has a unique Pst I restriction site at the 3'-end of the protein A gene fragment which will be utilized in the following step B5.

B2. Preparation of a DNA fragment containing the protein A gene

100 μg of plasmid pSPA5 from step G of Example I were cut with restriction enzyme Eco RI for 1 hr at 37° C. This produced two DNA fragments, viz. The inserted DNA fragment containing the protein A gene (2.1 kb) between positions 0.2 kb and 2.3 kb in FIG. 2B and the vector pHV14 (7.2 kb). This digest was heat inactivated, precipitated with ethanol, dissolved in 100 μl of TE and sedimented through a 10–30% sucrose gradient in TE buffer. A Beckman SW40 rotor was used at 5° C., 35,000 rpm, for 20 hrs. The gradient was fractionated into 0.5 ml fractions, each of which was analyzed by agarose gel electrophoresis. The fractions containing the 2.1 kb fragment were pooled, precipitated with 2 volumes of ethanol and dissolved in TE buffer. As appears from FIGS. 2A and B the fragment contains, in addition to the whole protein A gene, an *E. coli* sequence derived from plasmid pBR322 and a staphylococcal gene residue.

B3. Preparation of a DNA fragment containing part of the protein A gene

5 μg of the purified 2.1 kb fragment from step B2 were cut with restriction enzyme Sau 3A for 1 hr at 37° C. The digest was run on a preparative 8% polyacrylamide gel electrophoresis in TEB buffer. The gel was stained with ethidium bromide (1 μg/ml) and a DNA fragment of approximately 600 base pairs was cut out. This fragment corresponds to the part of the gene between positions 1.15 and 1.8 kb in FIG. 2B. The DNA was eluted overnight at 37° C. in 5 ml of TE+0.3M NaCl. The eluate was passed over a column containing approximately 300 μl of sedimented DE-52 (Whatman, England) equilibrated with 5 ml of TE. After a 2 ml wash with TE+0.3M NaCl the DNA was eluted with two volumes of each 0.5 ml of TE+0.6M NaCl. The eluate containing the DNA fragment was diluted with one volume of TE, precipitated with ethanol and dissolved in TEB buffer. The resulting purified protein A gene fragment has cohesive ends corresponding to a Sau 3A restriction site and an intermediate Hind III site.

B4. Preparation of vector plasmid pUR222

Plasmid pUR222 is a commercially available vector containing the gene coding for the enzyme β-galactosidase (lac Z). The gene comprises a multilinker having several restriction sites, such as Pst I, Bam H1 and Eco RI. Since β-galactosidase is easily detectable by enzymatic assays, recombinants having a DNA fragment inserted in one of the restriction sites can easily be scored with the use of appropriate host strains. Often Xgal plates are used (Xgal is a chromogenic substrate, 5-bromo-4-chloro-3-indolyl-β-D-galactoside, which releases a blue indolyl derivative when cleaved by β-galactosidase) upon which β-galactosidase negative recombinants appear as white colonies in contrast to the blue-green colour of colonies containing plasmids without an insert.

To cleave plasmid pUR222 in the β-galactosidase coding gene to provide cohesive ends complementary to the cohesive ends of the protein A fragment of step B3 for insertion thereof into the plasmid, the Bam H1 restriction site was used. 1 μg of pUR222, supplied by Boehringer-Mannheim, Germany, was digested with the restriction enzyme Bam H1 for 1 hr at 37° C., whereupon the enzyme was inactivated at 65° C. for 10 minutes. This cleavage preparation was used in the following step B5 for ligation with the protein A fragment.

B5. Construction of a hybrid plasmid pSPA10 containing pSPA2 and pTR262 (FIG. 7)

200 ng of pUR222 digested with Bam H1 as described in step B4 and 200 ng of eluted protein A fragment, as described in step B2, were mixed and ligated in a total volume of 20 μl overnight at +14° C. The enzyme was inactivated at 65° C. for 10 minutes, precipitated with ethanol and dissolved in TE buffer. The whole DNA-mixture, containing i.a. recombinant plasmids having the protein A insert in the β-galactosidase gene, was cut with restriction enzymes Hind III and Pst I for 1 hr at 37° C. in the recommended buffer for Hind III. This cleaves the recombinant plasmid in the β-galactosidase gene (Pst I) and in the protein A gene (Hind III) producing two fragments, viz. a small fragment consisting of a minor β-galactosidase DNA sequence linked to the part of the protein A gene fragment from the Sau 3A site at position 1.15 kb to the Hind III site in FIG. 2B, and a large fragment consisting of the rest of the recombinant plasmid, which comprises the major part of the β-galactosidase gene linked to the protein A gene fragment from the Hind III site to the Sau 3A site at position 1.8 kb in FIG. 2B. As appears from FIG. 7 the β-galactosidase fragment has an Eco RI restriction site close to the point of fusion with the protein A fragment (the Bam H1 site).

200 ng of plasmid pSPA2 from step B1 were cut with the restriction enzymes Hind III and Pst I in the same way as above to cleave the plasmid into (see FIG. 7) three fragments, viz. one fragment extending from the Hind III site located between the Tet-gene and the 5'-end of the protein A gene to the Hind III site within the protein A gene, a protein A gene fragment extending from the latter Hind III site to the Pst I site at the 3'-end of the protein A gene, and a larger fragment of pTR262 origin comprising the rest of the plasmid.

The two digests prepared above were inactivated at 65° C. for 10 minutes, mixed and precipitated with ethanol. The DNA was dissolved in ligation buffer and treated with T4-ligase. The desired recombinant plasmid comprises the above mentioned large fragment, obtained on cleavage of the pUR222 recombinant inserted in pSPA2 between the Hind III site within the protein A gene and the Pst I site and comprising the 5'-end of the protein A gene, one part thereof thus being derived from pSPA2 and the other originating from the pUR222 recombinant. Further, the plasmid is ampillicin and tetracycline resistant and should give blue colour on Xgal plates as will be explained below.

The ligated DNA-mixture was therefore used to transform *E. coli* RRI del M15. Cleavage, ligation and transformation were effected as described above. Recombinants were plated out on Xgal plates containing ampicillin and tetracycline. One of the clones appeared as light blue, and restriction analysis was performed on its plasmid. This revealed a plasmid, designated pSPA10 (FIG. 7), which consists of parts of plasmid pUR222, plasmid pTR262 and the protein A gene originating from plasmid pSPA1 and which has a unique Eco RI site at the downstream end of the gene.

Although plasmid pSPA10 does not contain the whole lac Z gene coding for β-galactosidase but only the gene coding for the α-fragment thereof (lac Z'), it is active in cleaving the Xgal substrate thereby producing blue colour under the above used conditions. This is due to a complementation between the α-fragment coded by the plasmid and a chromosomal gene product containing the carboxy terminal fragment of β-galactosidase resulting in an active enzyme. The *E. coli* RRI del M15 host strain used above has such chromosomal gene material and therefore complements the α-fragment produced by the pSPA10 plasmid to an active β-galactosidase molecule.

B6. Subcloning of the protein A coding gene into plasmid pBR322 for the construction of plasmid pSPA8 (FIG. 7)

1 µg of the purified 2.1 kb protein A fragment from step B2 was cut with restriction enzyme Taq I for 1 hr at 60° C. to cleave it within the DNA of staphylococcal origin. The enzyme was inactivated by extraction with an equal volume of phenol, followed by repeated ether extraction and finally the DNA was precipitated with ethanol and dissolved in TE buffer. 1 µg of plasmid pBR322 was cut with restriction enzymes Cla I and Eco RV (which cleave in the same way and thus provide complementary cohesive ends) for 1 hr at 37° C. in Bam H1 buffer and then heat inactivated for 10 minutes at 65° C. The DNA samples were mixed, ligated and used to transform E. coli HB101 as described above under Routine Methods. Transformants were streaked out on ampicillin (35 µg/ml). Colonies were picked on plates containing 10 µg/ml of tetracycline and 35 µg/ml of ampicillin, respectively. Transformants that grew on ampicillin but not on tetracycline were considered as recombinants. 4 colonies out of 12 of these recombinants were discovered to be protein A positive using the ELISA method described under Routine Methods. Restriction analysis in which purified plasmid was cut with one, two or three restriction enzymes were performed on one of these clones. The resulting restriction map of this plasmid, designated pSPA8, is shown in FIG. 7. The thus constructed plasmid lacks any E. coli promoter upstream of the protein A gene, the protein A gene fragment being preceded by its own staphylococcal promoter only. B7 Construction of plasmid pSPA16 (FIG. 8)

A second shuttle vector was constructed coding for a truncated protein A (i.e. lacking the X-region). The construction is schematically outlined in FIG. 8. 5 µg of plasmid pSPA10 from step B5 was cut with Eco RI and HindIII and a 0.4 kb fragment was cut out from a 5% polyacrylamid gel after electrophoresis. The fragment was eluted, and purified as described above under Routine Methods. 5 µg of plasmid pSPA8 from step B6 were treated in the same way and a 0.7 kb fragment was isolated and purified. Finally, 2 µg of plasmid pHV33 were digested with EcoRI, treated with alkaline phosphatase and mixed with the two purified DNA fragments. After treatment with T4-ligase the DNA was used to transform E. coli HB101. Cleavage, alkaline phosphatase treatment, ligation and transformation were performed as described above under Routine Methods. Restriction analysis of 12 ampicillin resistant clones revealed one clone containing plasmid pHV33 with a 1.1 kb insert in the EcoRI site. The plasmid, designated pSPA16, is schematically shown in FIG. 8. FIG. 9 shows the nucleotide sequence and the deduced amino acids preceding the stop codon of this truncated protein A gene. The mature protein lacking region X, thus produced, contains 274 amino acids giving a predicted molecular weight of 30,938. This truncated protein A molecule, which is schematically shown in FIG. 10, contains all the IgG-binding parts of protein A intact except the C-terminal part of region C.

II. Retransformation of shuttle vectors pSPA15 and pSPA16 into E. coli

The shuttle vectors pSPA15 and pSPA16 constructed in section I above were retransformed into E. coli HB101 with selection for ampcillin (amp) resistance (50 µg/ml) as in section I. Transformants were tested for protein A production by the ELISA-test described above under Routine Methods. Plasmid DNA was isolated from protein A positive clones containing the respective plasmids as also described above under Routine Methods.

III. Transformation of strains of S. aureus, S. xylosus and S. epidermidis

A. Preparation and transformation of protoplasts of S. aureus SA113

Different species and even strains of staphylococci contain different restriction and modification systems, and most strains carry several of them (cf. Stobberingh, E. E., and K. Winkler, J. Gen. Microbiol. 99: 359–367 (1977) and Sjöström J.-E. et al., J. Bacteriol. 133: 1144–1149 (1978)).

This causes problems when plasmid DNA isolated from E. coli is to be introduced into staphylococci by transformation.

To overcome the restriction problem a restriction deficient mutant of S. aureus 8325, called SA113, originally isolated by Iordanescu et al (J. Gen. Microbiol. 96: 277–281 (1976)) was therefore used for performing primary transformations in S. aureus of plasmid DNA isolated from E. coli HB101. The original strain SA113 is lysogenic for prophages ∅11, ∅12 and ∅13 and was furthermore lysogenized with phage 83A. The strain has the following standard phage type: 29/47/75/85/. To further decrease the restriction the protoplasts were heated at 56° C. for 30 seconds immediately before the addition of DNA (cf. Asheshov et al. J. Gen. Microbiol. 31: 97–107 (1963), and Sjöstroöm, J.-E., et al., Plasmid 2: 529–535 (1979)).

Methods and media for the preparation of the protoplasts were mainly as those described for Bacillus subtilis by Wyrick and Rogers, J. Bacteriol. 116: 456–465 (1973) as modified by Chang and Cohen, Mol. Gen. Genet. 168: 111–115 (1979). However, some modifications were introduced for staphylococci as described by Lindberg in J. Jeljaczewicz: Staphylococci and Staphylococcal Infections, Zbl. Bakt. Suppl. 10: 535–541; Gustav Fischer Verlag, Stuttgart-New York (1981) and Götz et al., J. Bacteriol. 145: 74–81 (1981).

Ten ml samples of S. aureus SA113 grown in Trypticase Soy Broth (BBL, Cockeysville, Md., U.S.A.) to the stationary phase (approx. $2 \times 10^9$ colony forming units per ml) were harvested and suspended to the same volume in a hypertonic buffered medium (HBM) consisting of 0.7M sucrose, 0.02M Na-maleate and 0.02M $MgCl_2$, pH 6.5 adjusted with NaOH, plus 43 g Difco Penassay broth powder (Difco Lab., Detroit, Mich., U.S.A.) per liter. Lysostaphin (Schwarz/Mann Orangeburg, N.Y., U.S.A.) and lysozyme (Sigma Chemical Co., St. Louis, Mo., U.S.A.) were added at 20 and 2000 µg/ml final concentrations, respectively, and the cell suspensions were incubated at 37° C. with gentle shaking. Lysozyme is not necessary for removal of the cell wall, but it helps to separate the protoplasts which like intact cells of staphylococci have a tendency to aggregate. This incubation was continued till the absorbancy at 540 nm became constant, which usually occurred within 3 hours. The remaining intact bacteria and cell debris were pelletted by centrifugation at $2,500 \times g$ for 10 min. The supernatants were collected and centrifuged again at $16,000 \times g$ for 10 min. The pelletted protoplasts were resuspended in HBM to 1/10 of the volume of the starting culture. 0.4 ml suspensions of the prepared SA113 protoplasts in HBM (approx. $2 \times 10^7$ cell wall regenerating protoplasts per ml) were transformed with E. coli plasmid DNA from step II above as follows.

10–20 μg of protein A positive plasmid DNA were added in a maximal volume of 20 μl with gentle mixing. Two milliliters of 40% PEG 6000 (stock solution of polyethylene glycol (PEG) prepared by dissolving 40 g of PEG with a molecular weight of 6,000 (PEG 6000) in 100 ml of hypertonic buffer (HB): 0.7M sucrose, 0.02M Na-maleate, and 0.02M MgCl₂, pH 6.5 adjusted with NaOH) was immediately added followed 2 minutes later by 8 ml of HBM. The suspension was centrifuged at 48,200×g for 15 min. The pelletted protoplasts were then resuspended in 1 ml of HBM and after appropriate dilutions in HBM samples were plated for regeneration of the cell wall. The regeneration medium was DM3, a Casamino Acids-yeast extract-bovine serum albumin medium containing 0.5M sodium succinate and 8 g agar per liter according to Chang and Cohen, Mol. Gen. Genet. 168: 111–115 (1979). For selection of chloramphenicol resistant transformants, CY-broth (Novick, R. P., J. Gen. Microbiol. 33: 121–136 (1963)) with 0.5M sodium succinate, 0.02M MgCl₂, 0.08% bovine serum albumin, and 4 g agar per liter was used as a soft agar overlay with chloramphenicol to give a final concentration of 10 μg/ml in the whole agar medium. Phenotypic expression was allowed at 37° C. for 3 hours before the addition of soft agar with chloramphenicol. The plates were incubated at 37° C. for 3 days. Chloramphenicol resistant transformants were restreaked on TSA-plates (Trypticase Soy Agar) with chloramphenicol (10 μg/ml).

B. Detection of protein A

A qualitative test of protein A was performed by streaking transformants on Brain-Heart-Infusion (BHI)-agar (Difco lab., Detroit, Mich., U.S.A.) plates with 1% dog serum. Protein A production was detected as a halo of precipitated IgG-protein A complex around the colonies (Kronvall, G. et al., J. Immunol. 104: 140 (1970)). The recipient strain S. aureus SA113 produced very low amounts of protein A, nearly without a detectable halo around the colonies.

C. Preparation of plasmid DNA

Plasmid DNA was prepared from the protein A producing SA113 transformants obtained in step A by a rapid boiling method as described by Holmes et al (Anal. Biochem. 114: 193 (1981)) except that lysozyme was replaced by lysostaphin at a final concentration of 50 μg/ml.

D. Transformation of staphylococci

The following staphylococcal strains were transformed with plasmids pSPA15 and pSPA16 as described above in step A for S. aureus SA113:

Staphylococcus aureus U320, a protein A negative mutant of strain S. aureus SA113 isolated at the Department of Microbiology, The Biomedical Centre, Uppsala, Sweden;

Staphylococcus epidermidis 247, a coagulase negative staphylococcus which does not produce protein A;

Staphylococcus xylosus KL117 a coagulase negative staphylococcus which does not produce protein A.

IV. Production of protein A coded by plasmids pSPA15 and pSPA16

Transformants obtained in steps IIIA and D above were grown in Trypticase Soy Broth enriched with thiamine (1 mg/liter), nicotinic acid (1.5 mg/liter), and Ca-pantothenate (1.5 mg/liter) and the production of extracellular as well as of cell wall bound protein A was determined. Cell wall bound protein A is the amount of protein A released after total lysis of 1 ml of washed cells in the stationary growth phase (approx. 8×10⁹ CFU/ml), and extracellular protein A is the amount of protein A in the growth medium.

Cell wall associated protein A was measured quantitatively by testing the binding of $^{125}$I-labelled human IgG to the cells (Kronvall, G., J. of Immunol. 104: 273–278 (1970)) or by using the ELISA-test as described under Routein Methods after complete lysis of the cells with lysostaphin.

Extracellular protein A was measured using the ELISA-test.

S. aureus strains Cowan I and A676 were used as reference strains for the production of cell wall bound and extracellular protein A, respectively.

Strain Cowan I has been the type strain for studies of cell wall bound protein A (Nordström K., Acta Universitatis Upsaliensis. Abstracts of Uppsala Dissertations from the Faculty of Medicine 271 (1977)). Small amounts of protein, i.e. extracellular protein A, were found in the growth medium, probably due to autolysis.

Strain A676 produces only extracellular protein A (Lindmark et al., Eur. J. Biochem. 74: 623–628 (1977)) and is used by Pharmacia AB for industrial production of protein A.

The results are presented in Tables 2 and 3 below. All values in the tables are corrected for cell densities and thus directly comparable.

TABLE 2

Production of cell wall bound protein A in different staphylcoccal species coded by plasmid pSPA15

| Bacterial strain | Cell wall bound protein A % | Extra-cellular protein A % |
|---|---|---|
| *Staphylococcus aureus:* | | |
| Cowan 1 | 100 | 12 |
| 113 | 1.5 | 0 |
| 113 (pSPA15) | 3 | 0.3 |
| U320 | 0 | 0 |
| U320 (pSPA15) | 50 | 6 |
| *Staphylococcus epidermidis:* | | |
| 247 | 0 | 0 |
| 247 (pSPA15) | 3 | 0.3 |
| *Staphylococcus xylosus:* | | |
| KL117 | 0 | 0 |
| KL117 (pSPA15) | 3 | 0.3 |

In Table 2 the amount of cell wall bound protein A in strain Cowan I is set as 100% corresponding to dilution 1/256 in the ELISA-test and equal to 120 mg protein A/liter lysostaphin treated culture. All other figures in the table refer to this figure.

TABLE 3

Production of extracellular protein A in different staphylococcal species coded by plasmid pSPA16

| Bacterial strain | Extra-cellular protein A % | Cell wall bound protein A % |
|---|---|---|
| *Staphylococcus aureus:* | | |
| A676 | 100 | 0 |
| 113 | 0 | 1.5 |
| 113 (pSPA16) | 3 | 1.5 |
| U320 | 0 | 0 |
| U320 (pSPA16) | 100 | 0 |
| *Staphylococcus epidermidis:* | | |
| 247 | 0 | 0 |
| 247 (pSPA16) | 12 | 0 |
| *Staphylococcus xylosus:* | | |
| KL117 | 0 | 0 |

TABLE 3-continued

Production of extracellular protein A in different staphylococcal species coded by plasmid pSPA16

| Bacterial strain | Extra-cellular protein A % | Cell wall bound protein A % |
|---|---|---|
| KL117 (pSPA16) | 25 | 0 |

In Table 3 the amount of protein A in the growth medium (i.e. extracellular protein A) is set as 100%, corresponding to dilution 1/256 in the ELISA-test and equal to 90 mg protein A/liter medium. All other figures in the table refer to this figure.

As appears from Tables 2 and 3 above the protein A coded by plasmid pSPA15 is essentially cell wall bound, whereas substantially all the truncated protein A coded by plasmid pSPA16, which lacks region X, is secreted into the growth medium.

Staphylococcus xylosus is used as a starter culture for the production of "Rohwurst" (Liepe, H.-U., Forum Mikrobiologie 5; 10–15 (1982), Fisher et al., Fleischwirtschaft 60: 1046–1051 (1980)) and thus might be considered as an apathogenic staphylococcal species. For this reason S. xylosus containing the cloned protein A gene would be an alternative to S. aureus for industrial production of protein A.

A protein A producing clone of Staphylococcus xylosus KL117 containing the plasmid pSPA16 has been deposited with the collection of the Deutsche Sammiung von Mikroorganismen (DSM), Grisebachstrasse 8, 3400 Gottingen, Federal Republic of Germany on Aug. 15, 1983 where it was assigned No. DMS 2706.

It is to be understood that the amounts of protein A produced in the above Examples are not maximum yields in any way. Thus, it is within the skill of any person skilled in the art to increase the yields, e.g. by a suitable choice of the nutrient medium etc.

In the following Examples the starting materials, buffers, cell media and routine method steps were as follows.

STARTING MATERIALS

Bacterial hosts.

Four strains of E. coli were used in the Examples: HB101, described by Boyer et al, J. Mol. Biol. 41, 459–472 (1969); XAC lac, (Miller et al, J. Mol. Biol., 109, 275–301 (1977); RRI del M15 (Langey et al, Proc. Natl. Acad. Sci., USA, 72, 1254–1257 (1975); JM 83 (Viera and Messig, Gene 19, 259–268 (1982)). Also S. aureus SA113, described by Iordanescu et al, J. Gen. Microbiol. 96: 277–281 (1976), was used. (The strains are available at the Department of Microbiology (N), Biomedical Centre, Uppsala, Sweden).

Cloning vehicles. The cloning vehicles used in the Examples were
pBR322 as constructed and described by Bolivar et al, Gene 2, 95–113 (1977);
pUR 222 as constructed and described by Rüther et al, Nucl. Acids Res., 9, 4087–4098 (1981);
PTR262 as constructed and described by Roberts, T. M. et al, Gene 12, 123–127 (1980);
pUC8 as constructed and described by Viera and Messig, Gene 19, 259–268 (1982);
pHV14 as constructed and described by Ehrlich, S. D., Proc. Natl. Acad. Sci. USA 70, 3240–3244 (1978);
pSKS104 and pSKS106 as constructed and described by Casadaban, M. J., Martinec-Arias, A., Shapiro, F., and Chou, J., Methods in Enzymology, 100, p. 293–308 (1983);
plasmids pSPA1, pSPA3, pSPA5 and pSPA16 containing the gene coding for staphylococcal protein A as constructed and described in the International patent application PCT/SE83/00297 (Swedish patent application 8204810-9). Cultures of an E. coli 259 strain containing plasmid pSPA1 and of an S. xylosus KL117 strain containing plasmid pSPA16 have been deposited with the Deutsche Sammlung von Mikroorganismen (DSM), Göttingen, Federal Republic of Germany, under No. DSM 2434 on July 12, 1982 and No. DSM 2706 on Aug. 15, 1983, respectively; Phage vectors M13 mp8 and mp9 RFI DNA, supplied by New England Biolabs, Beverly, Mass., U.S.A. (catalogue No. 408 and 409).

BUFFERS AND MEDIA

Tris-EDTA buffer ("TE"): 0.001M EDTA and 0.01M Tris (pH 7.8).
Coating buffer (carbonate-bicarbonate-pH 9.6): 1.59 g $Na_2CO_3$, 2.93 g $NaHCO_3$ and 0.2 g $NaN_3$, made up to 1 liter with distilled $H_2O$.
PBS TWEEN: (Phosphate buffered saline plus 0.05% TWEEN®): 8.0 g NaCl, 0.2 g $KH_2PO_4$, 2.9 g $Na_2HPO_4 \times 12\ H_2O$, 0.2 g KCl, 0.2 ml TWEEN® 20 and 0.2 g $NaN_3$, made up to 1 liter with distilled $H_2O$; pH 7.4
Diethanolamine buffer 10%: 97 ml diethanolamine, 800 ml distilled $H_2O$, 0.2 g $NaN_3$, and 100 mg $MgCl_2 \times 6H_2O$; pH adjusted to 9.8 with 1M HCl; made up to 1 liter with distilled $H_2O$
Luria-broth ("LB"): 10 g Difco tryptone, 5 g Difco yeast extract, 0.5 g NaCl, 2 ml 1M NaOH; adjusted to pH 7.0 with 1M NaOH; 10 ml 20% glucose added after autoclaving.
LA-medium: Luria broth supplemented with 1% Difco agar
TEB buffer: 0,09M TRIS-borate, 0,09M boric acid and 0,002M EDTA.
ONPG buffer: 2 mM o-nitrophenyl-β-D-galactoside (ONPG, Sigma product No. N-1127) in 0.1M potassium phosphate buffer, pH 7.3, containing 0.1M 2-mercaptoethanol and 1 mM $MgCl_2$.
Xgal-medium: LA-medium supplemented with 40 mg/l of 5-bromo-4-chloro-3-indolyl-β-D-galactoside (Xgal).
AXI: LA-medium supplemented with 50 mg/l of ampicillin, 40 mg/l of 5-bromo-4-chloro-3-indoyl-β-D-galactoside (Xgal) and 0.1 mM isopropyl-β-D-thiogalactoside (IPTG).

ROUTINE METHODS

Certain procedures were carried out repeatedly in the Examples. Unless otherwise specified, they were done exactly as follows each time that they were carried out.

Transformations. Transformation of E. coli K 12 with plasmid DNA, was performed exactly as described by Morrison, D. A., Methods in Enzymology, Academic Press 68, 326–331 (1979). The transformed cells were selected in a conventional manner on plates by plating for single colonies on LA plates containing suitable antibiotics, i.e. 35 μg/ml of ampicillin or 25 μg/ml of chloroamphenicol.

Isolation of plasmids. Large scale plasmid preparation was performed exactly as described by Tanaka, T. and Weisburn, B., J. Bacteriol. 121, 354–362 (1975). For scoring a large number of clones for plasmids the "mini alkali method" was used exactly as described by Birnboim, H. C. and Doly, J., Nucl. Acids Res. 7, 1513–1523 (1979).

Gel elution. DNA fragments were eluted from either polyacrylamide or agarose gel pieces exactly as described by Maxam et al, P.N.A.S. 74, 560–564 (1977).

DNA sequencing. DNA fragements were 5'-end labelled, and their DNA sequences were determined exactly as described by Maxam et al, supra. The 5'-end of endonuclease generated DNA fragments was labelled with ($\gamma$-$^{32}$P) ATP (New England Nuclear, USA; 2700 Ci/mmol) using T4 polynucleotide kinase (Boehringer, Mannheim, West Germany).

Restriction enzyme digestion of DNA. DNA was cleaved with conventional restriction enzymes purchased from New England Biolabs, Beverly Mass., U.S.A. The restriction enzymes were added to DNA at conventional concentrations and temperatures and with buffers as recommended by New England Biolabs.

Ligating DNA fragments. All DNA fragments were ligated at 14° C. over-night with T4 DNA ligase purchased from New England Biolabs, Beverly Mass., U.S.A., in a buffer recommended by the supplier.

Agarose gel electrophoresis. 0.7% agarose gel electrophoresis for separating cut plasmid fragments, supercoiled plasmids, and DNA fragments 1000 to 10,000 nucleotides in length was performed exactly as described by Helling et al, J. Vir. 14, 1235–1244 (1974).

Polyacrylamide gel electrophoresis. 8% polyacrylamide gel electrophoresis for the separation of DNA fragments 100 to 4000 nucleotides in length was performed exactly as described by Maxam et al, P.N.A.S. 74, 560–564 (1977).

Preparation of cell lysate for detection of protein A. E. coli clones were grown overnight at 37° C. in 50 ml Luria-broth (LB) with ampicillin added at 35 $\mu$g/ml. After centrifugation the cells were resuspended in 5 ml Tris-EDTA (0.05M. pH 8.5, 0.05M) and centrifuged. The cells were resuspended in 5 ml of the same buffer and lysozyme was added to a final concentration of 2 mg/ml. After 1 hour at 37° C. the lysate was centrifuged in a Sorvall SS-34 rotor at 15,000 rpm for 15 minutes. The supernatant was collected and assayed for protein A.

Detection and quantification of protein A from E. coli clones. An ELISA-test (enzyme linked immunosorbent assay) was used for detection and quantification of produced protein A. The test makes use of a special microtiter plate (Titertek, Amstelstad, the Netherlands) having no net charge (neutral), the wells of which are coated with human IgG (Kabi, Sweden). Test samples are then added to allow protein A to bind to the Fc-part of the IgG-molecules. The amount of remaining free Fc-sites is then titrated by adding alkaline phosphatese linked to protein A. After washing of the wells, p-nitrophenyl-phosphate is added as a substrate for alkaline phosphatase.

Assay: The wells of a microtiter plate were filled with 50 $\mu$l of a solution of human IgG (Kabi, Sweden) at 500 $\mu$g/ml in a coating buffer and the plate was incubated at room temperature for 1 hour. The wells were then washed three times with PBS+0.05% Tween® 20, which was used in all washes in the assay, and 50 $\mu$l of the lysate to be tested was added. For quantitative determinations twofold serial dilutions of the lysates in PBS+0.05% Tween® 20 were made. 10 $\mu$l of PBS+0.1% Tween® 20 was then added and incubation was allowed for 1 hour at room temperature. The wells were again washed three times, and 50 $\mu$l of protein A-alkaline phosphatase conjugate (prepared exactly as described in Immunochemistry, Pergamon Press 1969, Vol. 6 pp. 43–52) was added. After 1 hour of incubation at room temperature the wells were again washed three times and 100 $\mu$l of alkaline phosphatase substrate (Sigma 104=p-nitrophenylphosphate at 1 mg/ml) was added. The enzyme reaction was interrupted after 30 minutes by the addition of 10 $\mu$l of 3M NaOH. The results was determined visually. A positive result, i.e. presence of protein A, is a colour-less reaction mixture, since no free Fc-sites of IgG are available to bind the conjugate. A negative result, i.e. no protein A, is observed as a yellow colour due to the activity of the alkaline phosphatase of the bound conjugate. Quantitative determinations of protein A were made by running serial twofold dilutions of a protein A standard solution of known concentration in parallel with the test samples. Tween® and Tween-20® are polyoxyethylene derivatives of fatty acid partial esters of sorbitol anhydrides $\beta$-galactosidase assay Recombinants containing a functional lac Z gene were scored by plating on Xgal medium. Cell free $\beta$-galactosidase activity was assayed by a colorimetric procedure using o-nitrophenyl-$\beta$-D-galactoside (ONPG, Sigma product No. N-1127) as substrate as described by Miller, J. H., Experiments in Molecular Genetics, Cold Spring Harbor, N.Y.; Cold Spring Harbor Laboratory, 1972, with the following modifications. The assay was performed at +8° C. and the activity was measured at 405 nm. One unit of activity represents the change in absorbance at 405 nm per minute. $\beta$-galactosidase activities of the fused proteins coupled to IgG-Sepharose® were determined at 8° C., inverting the tube in order to prevent sedimentations.

Phage M13 cloning and sequencing.

All M13 cloning, purifications and sequencing was performed as described in the Instructions/Protocol obtained by the supplier (New England Biolabs, Beverly, Mass., U.S.A., catalogue No. 408 and 409).

EXAMPLE I

I. Analysis of the DNA Sequence of the Protein A Gene

In order to make fusions between genes or gene parts it is desirable to know the DNA sequence and its deduced amino acid sequence around the fusion point of the two genes or gene parts to be fused. With the knowledge thereof it will be possible to predict how the linkage should be designed in order to give the correct reading frame in both genes or gene parts and thus possibly the expression of a functional hybrid protein.

In our Swedish patent application No. 8204810-9 (the disclosure of which is incorporated herein by reference) the construction of three plasmids containing the whole structural gene coding for staphylococcal protein A is described, viz. plasmids pSPA1, pSPA3 and pSPA5. However, only the DNA sequence of the 5'-end of the protein A gene (regions S, E, D and part of A in present FIG. 2A) is disclosed. A preliminary sequence of the whole protein A gene was therefore determined in order to obtain more detailed information of the DNA sequence in the 3'-end of the gene. This sequencing operation was effected as described above under Routine Methods, the DNA source being purified plasmid pSPA3, which is the smallest of the three protein A gene containing plasmids and therefore the least difficult one to sequence. In FIG. 12 the obtained DNA sequences around the Sau 3A restriction site at position 1,8 kb and around the Pst I restriction site at position 2,1 kb in the protein A gene restriction map of FIG. 2B are shown together with the corresponding deduced amino acid sequence. The particular interest in the above two restriction sites for the present purposes will be explained below.

Based upon the DNA sequence obtained it was decided to construct two different gene fusion vectors by inserting an M 13 multilinker (an oligonucleotide containing restriction sites for several restriction enzymes) into the above mentioned Sau 3A site nucleotide 1096 of FIG. 12 and the Pst I site at nucleotide 1541 of FIG. 12. These sites are located before and after the repetetive part of region X of the protein A gene (FIG. 2A) which is thought to be involved in the binding of protein A to the peptidoglycan of the cell wall in *S. aureus*. The possible influence thereof on the fused proteins to be produced on expression of genes fused by means of such fusion vectors could then be determined. The construction of the two gene fusion vectors is described hereinafter.

II. Construction of Fusion Vector Plasmid pSPA11 (FIG. 13A)

In the following steps A-E the construction of a plasmid containing the protein A gene without region X and having a unique Eco RI site inserted at the Sau 3A site at position 1098 (FIG. 12) is described.

A. Subcloning of the 5'-end of the protein A gene from pSPA1 into plasmid pTR262 to obtain plasmid pSPA2 (FIG. 7)

1 μg of plasmid pSPA1 (see FIG. 1) and 1 μg of plasmid pTR262 were cut with restriction enzymes Hind III and Pst I, mixed, treated with T4-ligase and used to transform *E. coli* HB101. Cleavage, ligation and transformation were effected as described under Routine Methods.

Plasmid pTR262 contains a lambda repressor gene which on expression inactivates the gene for tetracycline resistance. The lambda repressor gene has a Hind III site and insertion of a DNA sequence into the latter therefore inactivates the lambda repressor gene and activates the tetracycline resistance gene. Plasmid pTR262 thus permits positive selection for tetracycline resistant recombinants.

Colonies containing recombinants were thus selected as being tetracycline resistant. 1 colony out of 20 of these recombinants was discovered to be protein A positive using the ELISA method described under Routine Methods. Restriction analysis indicated that it contained vector plasmid pTR262 having a 2.1 kb protein A gene insert derived from the fragment corresponding to 0.0 to 2.1 kb of the pSPA1 restriction map of FIG. 1 and 2B. This plasmid was designated pSPA2 and is shown schematically in FIG. 7. It has a unique Pst I restriction site at the 3'-end of the protein A gene fragment which will be utilized in the following step E.

B. Preparation of a DNA fragment containing the protein A gene

100 μg of plasmid pSPA5 (plasmid vector pHV14 having a protein A gene insert; see Starting Materials above) were cut with restriction enzyme Eco RV for 1 hr at 37° C. This produced two DNA fragments, viz. the inserted DNA fragment containing the protein A gene (2.1 kb) between positions 0.2 kb and 2.3 kb in FIG. 2B and the vector pHV14 (7.2 kb). This digest was heat inactivated, precipitated with ethanol, dissolved in 100 μl of TE and sedimented through a 10-30% sucrose gradient in TE buffer. A Beckman SW40 rotor was used at 5° C., 35,000 rpm, for 20 hrs. The gradient was fractionated into 0.5 ml fractions, each of which was analyzed by agarose gel electrophoresis. The fractions containing the 2.1 kb fragment were pooled, precipitated with 2 volumes of ethanol and dissolved in TE buffer. As appears from FIGS. 2A and B the fragment contains, in addition to the whole protein A gene, an *E. coli* sequence derived from plasmid pBR322 and a staphylococcal gene residue.

C. Preparation of a DNA fragment containing part of the protein A gene

5 μg of the purified 2.1 kb fragment from step B were cut with restriction enzyme Sau 3A for 1 hr at 37° C. The digest was run on a preparative 8% polyacrylamide gel electrophoresis in TEB buffer. The gel was stained with ethidium bromide (1 μg/ml) and a DNA fragment of approximately 600 base pairs was cut out. This fragment corresponds to the part of the gene between positions 1.15 and 1.8 kb in FIG. 2B. The DNA was eluted overnight at 37° C. in 5 ml of TE+0.3M NaCl. The eluate was passed over a column containing approximately 300 μl of sedimented DE-52 (Whatman, England) equilibrated with 5 ml of TE. After a 2 ml wash with TE+0.3M NaCl the DNA was eluted with two volumes of each 0.5 ml of TE+0.6M NaCl. The eluate containing the DNA fragment was diluted with one volume of TE, precipitated with ethanol and dissolved in TE buffer. The resulting purified protein A gene fragment has cohesive ends corresponding to a Sau 3A restriction site and an intermediate Hind III site.

D. Preparation of vector plasmid pUR222

Plasmid pUR222 is a commercially available vector containing the gene coding for the enzyme β-galactosidase (lac Z). The gene comprises a multilinker having several restriction sites, such as Pst I, Bam H1 and Eco RI. Since β-galactosidase is easily detectable by enzymatic assays, recombinants having a DNA fragment inserted in one of the restriction sites can easily be scored with the use of appropriate host strains. Often Xgal plates are used (Xgal is a chromogenic substrate, 5-bromo-4-chloro-3-indolyl-β-D-galactoside, which releases a blue indolyl derivative when cleaved by β-galactosidase) upon which β-galactosidase negative recombinants appear as white colonies in contrast to the blue-green colour of colonies containing plasmids without an insert.

To cleave plasmid pUR222 in the β-galactosidase coding gene to provide cohesive ends complementary to the cohesive ends of the protein A fragment of step C for insertion thereof into the plasmid, the Bam H1 restriction site was used. 1 μg of pUR222, supplied by Boehringer-Mannheim, Germany, was digested with the restriction enzyme Bam H1 for 1 hr at 37° C., whereupon the enzyme was inactivated at 65° C. for 10 minutes. This cleavage preparation was used in the following step E for ligation with the protein A fragment.

E. Construction of a hybrid plasmid pSPA10 containing pSPA2 and pTR262 (FIG. 7)

200 ng of pUR222 digested with Bam H1, as described in step D, and 200 ng of eluted protein A fragment, as described in step C, were mixed and ligated in a total volume of 20 μl overnight at +14° C. The enzyme was inactivated at 65° C. for 10 minutes, precipitated with ethanol and dissolved in TE buffer. The whole DNA-mixture containing i.a. recombinant plasmids having the protein A insert in the β-galactosidase gene was cut with restriction enzymes Hind III and Pst I for 1 hr at 37° C. in the recommended buffer for Hind III. This cleaves the recombinant plasmid in the β-galactosidase gene (Pst I) and in the protein A gene (Hind III) producing two fragments, viz. a small fragment consisting of a minor β-galactosidase DNA sequence linked to the part of the protein A gene fragment from the Sau 3A site at position 1.15 kb to the Hind III site in FIG. 2B, and a large fragment consisting of the rest of the recombinant plasmid, which comprises the major part of the β-galactosidase gene linked to the protein A gene fragment from the Hind III site to the Sau 3A site at position 1.8 kb in FIG. 2B. As appears from FIG. 7 the β-galactosidase fragment has an Eco RI restriction site close to the point of fusion with the protein A fragment (the Bam H1 site).

200 ng of plasmid pSPA2 from step A were cut with the restriction enzymes Hind III and Pst I in the same way as above to cleave the plasmid into (see FIG. 7) three fragments, viz. one fragment extending from the Hind III site located between the Tet-gene and the 5'-end of the protein A gene to the Hind III site within the protein A gene, a protein A gene fragment extending from the latter Hind III site to the Pst I site at the 3'-end of the protein A gene, and a larger fragment of pTR262 origin comprising the rest of the plasmid.

The two digests prepared above were inactivated at 65° C. for 10 minutes, mixed and precipitated with ethanol. The DNA was dissolved in ligation buffer and treated with T4-ligase. The desired recombinant plasmid comprises the above mentioned large fragment, obtained on cleavage of the pUR222 recombinant, inserted in pSPA2 between the Hind III site within the protein A gene and the Pst I site and comprising the 5'-end of the protein A gene, one part thereof thus being derived from pSPA2 and the other originating from the pUR222 recombinant. Further, the plasmid is ampicillin and tetracycline resistant and should give blue colour on Xgal plates as will be explained below.

The ligated DNA-mixture was therefore used to transform *E. coli* RRI del M15. Cleavage, ligation and transformation were effected as described above. Recombinants were plated out on Xgal plates containing ampicillin and tetracycline. One of the clones appeared as light blue, and restriction analysis was performed on its plasmid. This revealed a plasmid, designated pSPA10 (FIG. 7), which consists of parts of plasmid pUR222, plasmid pTR262 and the protein A gene originating from plasmid pSPA1. In plasmid pSPA10 the protein A gene fragment is fused to the lac Z' gene through its Sau 3A site at position 1096 as appears from FIG. 15.

Although plasmid pSPA10 does not contain the whole lac Z gene coding for β-galactosidase but only the gene coding for the α-fragment thereof (lac Z'), it is active in cleaving the Xgal substrate thereby producing blue colour under the above used conditions. This is due to a complementation between the α-fragment coded by the plasmid and a chromosomal gene product containing the carboxy terminal fragment of β-galactosidase resulting in an active enzyme. The *E. coli* RRI del M15 host strain used above has such chromosomal gene material and therefore complements the α-fragment produced by the pSPA10 plasmid to an active β-galactosidase molecule.

The above described steps A–E thus produced a plasmid vector pSPA10 containing a desired protein A fragment which has a unique Eco RI site adjacent to its downstream end. In order to construct a convenient fusion vector a DNA-linker containing multiple restriction sites was introduced at that site simultaneously with removal of the non-desired fragment (containing the lac Z' gene and the gene for ampicillin resistance) between the Eco RI and Pst I sites, as will be described in the following section III.

F. Construction of fusion vector plasmid pSPA11 containing a multi-linker from phage M 13 mp 8 (FIG. 13A).

1 μg of plasmid pSPA10 from step E and 2 μg of phage vector M13 mp 8 (supplied by New England Biolabs, Beverly, Mass., USA) were cut separately with the restriction enzyme Eco RI, precipitated and dissolved in an appropriate buffer for the restriction enzyme Pst I. Digestion with the Pst I enzyme was performed and the two DNA digests were mixed, ligated and used to transform *E. coli* HB101. Cleavage, ligation and transformation were effected as described above under Routine Methods. The desired recombinants were selected as being tetracycline resistant and ampicillin sensitive. 52 tetracycline resistant clones were picked onto plates containing ampicillin. 3 of these clones were found to be ampicillin sensitive and restriction analysis on one of them revealed the plasmid schematically shown in FIG. 13A. This plasmid, which contains an inserted M13 multi-linker at the end of region C of the protein A gene (position 1.8 kb, FIG. 2B), was designated pSPA11. The deduced amino acid sequence is also indicated providing a guide for obtaining the correct reading frame after gene fusions. Plasmid pSPA11 is a vector well suited for gene fusions with the protein A fragment as will be demonstrated in the following step III.

III. Fusion of Plasmid pSPA11 to the *E. coli* Lac Z Gene

Figure 16A:
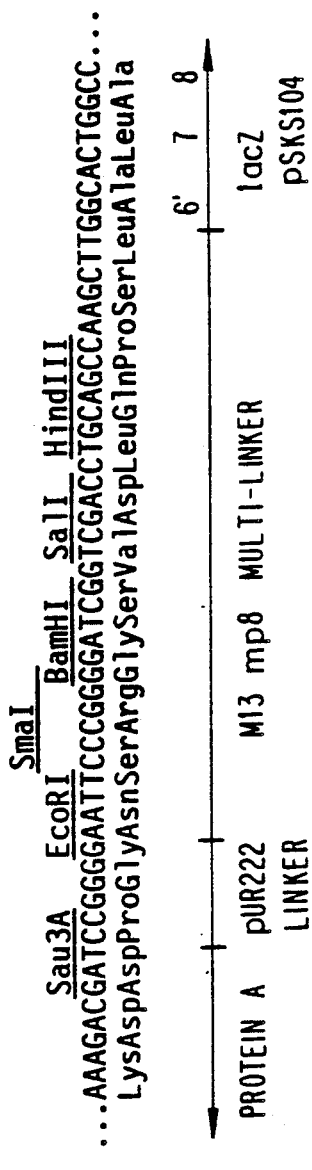

1 μg of plasmid pSKS104 (containing a unique *E. coli* RI site) was digested with the restriction enzyme Eco RI. This plasmid, together with the plasmid pSKS106 used below, are examples of a set of plasmids constructed to aid gene fusions between the *E. coli* lac Z gene and other genes. The hybrid protein produced by such fusions contains, at its carboxyterminus, enzymatically active β-galactosidase (minus a few amino acids at the N-terminus) and can be assayed by the enzymatic activity thereof. 1 μg of plasmid pSPA11 from step 2F (also having a unique Eco RI site) was digested separately with restriction enzyme Eco RI. Both DNA digests were heat inactivated, mixed, ligated and used to transform *E. coli* XAC lac (which strain lacks the β-galactosidase gene) as described above. Recombinants were scored on Xgal plates containing both tetracycline and ampicillin. Approximately half of these clones were light blue (the cleaved pSKS104 can be inserted in correct or wrong direction with equal probability) and restriction analysis on one of these revealed the plasmid schematically represented in FIG. 14A. This plasmid, designated pSPA13, contains the lac Z gene fused to the protein A gene at the nucleotide of position 1.8 kb in FIG. 2B. This is schematically shown in FIG. 15 and the deduced amino acid sequence over the fusion point is shown in FIG. 16A. Cultures of this clone have been deposited on Feb. 4, 1983 with the collection of the Deutsche Sammlung von Mikroorganismen (DSM), Göttingen, Federal Republic of Germany, where it was assigned No. DSM 2591.

IV. Fusion of Plasmid pSPA2 to the E. coli Lac Z Gene

Plasmid pSPA2, as constructed in step IIA above and shown in FIG. 7, contains a unique Pst I site at position 1541 of the protein A gene (see FIG. 15). This plasmid was therefore used for gene fusion of the corresponding protein A gene fragment to the lac Z gene of plasmid pSKS106.

Figure 16B:
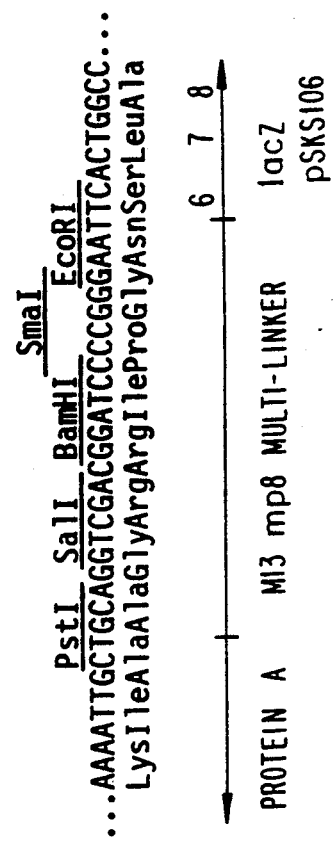

1 μg of plasmid pSPA2 from step IIA and 1 μg of plasmid pSKS106 were cut separately with restriction enzyme Pst I. The resulting DNA-fragments were mixed, ligated and used to transform E. coli XAC lac as described under Routine Methods. Recombinants were scored on Xgal plates containing tetracycline and ampicillin. As in section III above approximately half of these clones were light blue and restriction analysis on one of these revealed a plasmid schematically represented in FIG. 14B. This plasmid, designated pSPA14, contains the lac Z gene fused to the protein A gene at position 2.1 kb in FIG. 2B. This is schematically shown in FIG. 15, and the deduced amino acid sequence over the fusion point is shown in FIG. 16B. Cultures of this clone have been deposited on Feb. 4, 1983 with the collection of the Deutsche Sammlung von Mikroorganismen (DSM), Göttingen, Federal Republic of Germany, where it was assigned No. DSM 2592.

V. Construction of Fusion Vector Plasmid pSPA12 (FIG. 13B)

In order to make fusions of the protein A gene fragment of plasmid pSPA2 more generally possible a corresponding fusion vector as pSPA11 above was constructed by cutting out the lac Z gene from plasmid pSPA14 and retaining the multi-linker sequence preceding the 5'-end of the gene.

This was achieved by cutting 1 μg of plasmid pSPA14 from section IV with restriction enzyme Eco RI, ligating and transforming E. coli XAC lac as described above under Routine Methods and scoring for tetracycline resistance and lack of β-galactosidase activity. Clones were plated on Xgal plates containing tetracycline. Approximately 80% of these colonies were white and restriction analysis on one of these revealed a plasmid schematically shown in FIG. 13B. This plasmid, designated pSPA12, contains the M13 multi-linker at position 2.1 kb in FIG. 2B. The reading frame at the fusion point is shown in FIG. 13B.

VI. Subcloning of the Whole Protein A Coding Gene into Plasmid pBR322 for Construction of Plasmid pSPA8 (FIG. 7)

The above constructed fusion vectors pSPA11 and pSPA12 and the corresponding fused genes containing plasmids pSPA13 and pSPA14 all lack any E. coli residues upstream of the protein A gene originating from starting plasmid pSPA1, including the E. coli promoter. In order to construct, for comparative purposes, a plasmid which contains the whole structural gene of protein A, including the protein A promoter sequence, but which lacks any E. coli promoter upstreams thereof, the 2.1 kb protein A fragment from step IIB above was cloned into the plasmid vector pBR322 as follows below.

1 μg of the purified 2.1 kb protein A fragment from step IIB was cut with restriction enzyme Taq I for 1 hr at 60° C. to cleave it within the DNA of staphylococcal origin. The enzyme was inactivated by extraction with an equal volume of phenol, followed by repeated ether extraction, and finally the DNA was precipitated with ethanol and dissolved in TE buffer. 1 μg of plasmid pBR322 was cut with restriction enzymes Cla I and Eco RV (which cleave in the same way and thus provide complementary cohesive ends) for 1 hr at 37° C. in Bam H1 buffer and then heat inactivated for 10 minutes at 65° C. The DNA samples were mixed, ligated and used to transform E. coli HB101 as described above under Routine Methods. Transformants were streaked out on ampicillin (35 μg/ml). Colonies were picked on plates containing 10 μg/ml of tetracycline and 35 μg/ml of ampicillin, respectively. Transformants that grew on ampicillin but not on tetracycline were considered as recombinants. 4 colonies out of 12 of these recombinants were discovered to be protein A positive using the ELISA method described under Routine Methods. Restriction analysis in which purified plasmid was cut with one, two or three restriction enzymes were performed on one of these clones. The resulting restriction map of this plasmid, designated pSPA8, is shown in FIG. 7. The thus constructed plasmid lacks any E. coli promoter upstream of the protein A gene. The protein A gene fragment is preceded by its own staphylococcal promoter only.

VII. Detection and Quantitation of Protein A from E. coli Clones

To evaluate the protein A activity of the two plasmids pSPA13 and pSPA14 constructed above, comparisons were made with plasmid pSPA8 from section VI above, containing the whole structural protein A gene, and plasmid pSKS106, containing the β-galactosidase gene, with regard to total content of protein A and ability to bind to IgG-Sepharose ® columns as follows.

Cell suspensions of 300 ml carrying plasmids pSKS105, pSPA8, pSPA13 and pSPA14, respectively, were separately grown to $OD_{550}=1.0$ in LB medium containing 35 μg/ml of ampicillin without added glucose. Each cell culture was then centrifuged at 6000 rpm with a Sorvall GSA-rotor for 10 min. and the cell pellets were washed in 20 ml of TE (0.05M tris, pH 8.5, 0.05M EDTA) and again centrifuged as above. Finally the cell pellets were resuspended in 15 ml of a protease inhibitor buffer [0.02M potassium phosphate, pH 7.5, 0.1M NaCl, 0.5% sodium deoxycholate, 1% Triton X-100, 0.1% sodiumdodecyl sulfate (SDS), and 1 mM phenylmethylsulfonyl fluoride (PMSF)]. The cells were then sonicated in an MSE Sonicator for 3×30 sec. on an ice-bath and centrifuged at 15,000 rpm (Sorvall SS-34 rotor) for 10 min.

3 ml of supernatant was passed over an IgG-Sepharose ® 4B column (Pharmacia AB, Uppsala, Sweden), as described by Hjelm et al, FEBS Lett. 28 (1972), that had been equilibrated with PBST buffer. The column was then washed with PBST and the adsorbed proteins were eluted with 3 ml glycine buffer (0.1M glycine, 2% NaCl, pH 3.0). The eluate was dialyzed overnight against PBST and the concentration of protein A was determined by the ELISA-test as described in Routine Methods.

In order to determine whether any of the cultures contained a protein A—β-galactosidase fusion protein a modification of the test was performed. Before the addition of the protein A—alkaline phosphatase conjugate 100 μl of ONPG buffer was added to the wells of the microtiter plate and the colour change from colourless to yellow indicating β-galactosidase activity was determined visually. After three washes with PBST 50 μl of protein A—alkaline phosphatase conjugate was added and the test was continued exactly as described in Routine Methods. The results are shown in the following Table 1.

TABLE 1

| Plasmid | β-galactosidase activity | | Protein A concentration (μg/ml) | |
|---|---|---|---|---|
| | Total | Eluate | Total | Eluate |
| pSKS106 | — | — | 0 | 0 |
| pSPA8 | — | — | 16 | 16 |
| pSPA13 | + | — | 4 | 4 |
| pSPA14 | + | — | 1 | 1 |

In the Table "Total" gives the value for cell lysate and "Eluate" gives the corresponding value after binding and elution from IgG-Sepharose ®. As to the β-galactosidase activity a negative result represents no detectable colour change after incubation for 30 minutes at room temperature, whereas a positive result represents a clearly visible colour change after 5 minutes under the same conditions.

The test shows that the β-galactosidase from the control (pSKS106) does not bind to IgG coated wells in detectable amounts. In contrast, fusion proteins from cultures containing plasmids pSPA13 and pSPA14 bind to the wells and have enzymatic activity. The β-galactosidase activity is, however, not recovered after elution from the IgG-Sepharose ® column with glycine-buffer (see Table 1). This is due to inactivation of the enzyme in glycine buffers under pH 4.

The ELISA-test shows that the protein A concentrations of the three protein A containing clones (pSPA8, pSPA13 and pSPA14) vary although the same protein A gene sequence with the same promoter was used. The two clones having the lac Z gene fused to the protein A gene (pSPA13 and pSPA14) contain less protein A than the pSPA8 clone. However, the protein A of the protein A containing clones (pSPA8, pSPA13 and pSPA14) binds to IgG-Sepharose ® and can be eluted with high efficiency with glycine buffer of pH 3.0, as appears from Table 1, although the β-galactosidase of pSPA13 and pSPA14 is irreversibly inactivated.

In accordance with the above results desired enzymes may in this way be immobilized directly to an IgG affinity column from a cell crude lysate. Thus the specific affinity between IgG and protein A assures a one-step procedure giving a pure and immobilized enzyme.

VIII. Detection and Quantitation of β-galactosidase Activity from *E. coli* Clones after Immobilisation to IgG-Sepharose ®

Cells carrying plasmids pSKS106, pSPA8, pSPA13 and pSPA14 were grown and lysed exactly as described in section VII. 10 ml of supernatants were mixed with 1 ml of sedimented IgG-Sepharose ® 4B (Pharmacia AB, Uppsala, Sweden) that had been washed with PBST buffer. The mixtures were slowly inverted at 8° C. for 1 h and the supernatants were collected. After 4 washes with 12 ml of PBST the supernatants of the last wash were collected. The Sepharose ® was resuspended in 10 ml of PBST and aliquots were transferred to smaller tubes. The β-galactosidase activities were measured exactly as described in Routine Methods and the results are shown in the following Table 2.

TABLE 2

| Plasmid | total β-galactosidase* activity (units/ml) | % activity in supernatant | % activity in wash | % activity immobilized |
|---|---|---|---|---|
| pSKS106 | 14 | 84.9 | 0.1 | 0.2 |
| pSPA8 | 0 | N.D. | N.D. | N.D. |
| pSPA13 | 0.4 | 3.0 | 0.3 | 71.6 |
| pSPA14 | 0.1 | 6.0 | 0.0 | 78.4 |

*Values are calculated per ml of cell lysate
1 unit is defined as described under Routine Methods above.
N.D. = not detected The β-galactosidase from cells containing plasmid pSKS106 (control) does not bind to IgG-Sepharose ®, in accordance with the inability to bind to IgG coated wells (see step VII). In contrast, β-galactosidase from the cells containing plasmids pSPA13 and pSPA14 (protein A fusion proteins) binds efficiently, in fact more than 70% of the activity is immobilized.

From Table 2 it appears that the fusion protein lacking the non-IgG-binding region of the protein A molecule (X in FIG. 2) as produced through plasmid pSPA13 gives 3–4 times more fusion product than the corresponding fusion product containing substantially the whole protein A gene, as obtained via plasmid pSPA14. It seems that in this particular case the "spacer" region X is less favourable.

IX. Elution of Bound β-galactosidase-protein A-fusion Protein from IgG-Sepharose ®

Aliquots of IgG-Sepharose ® suspension with bound fusion proteins from step VIII were transferred to columns. The fusion proteins were eluted from 50 μl of sedimented gel by adding 0,5 ml buffer containing purified protein A (Pharmacia, Uppsala, Sweden) at various concentrations at room temperature. The β-galactosidase activity of the eluates and the IgG-Sepharose ® gels after elution were determined as described under Routine Methods above. The results are shown in Table 3, the values being expressed as percent of Sepharose ®-bound β-galactosidase activity.

TABLE 3

| | pSPA13 | | pSPA14 | |
|---|---|---|---|---|
| Buffer | immobilized after elution | eluate | immobilized after elution | eluate |
| PBST | 91 | 0 | 89 | 0 |
| PBST + 0,5 mg protein A | 63 | 35 | 62 | 30 |
| PBST + 2 mg protein A | 31 | 64 | 45 | 51 |

From the above results it appears that at least half the β-galactosidase activity may be eluted by this procedure.

EXAMPLE II

I. Construction of a Shuttle Plasmid Containing a Fusion Between the Genes Encoding Protein A and IGF-1

In the following steps A-D the construction of a plasmid pUN201, containing the protein A gene, without region X, fused to a synthetic gene encoding a modified human IGF-1 (human insulin-like growth factor type 1), is described.

A. Synthesis and cloning of the gene encoding human IGF-1

Figure 21B:
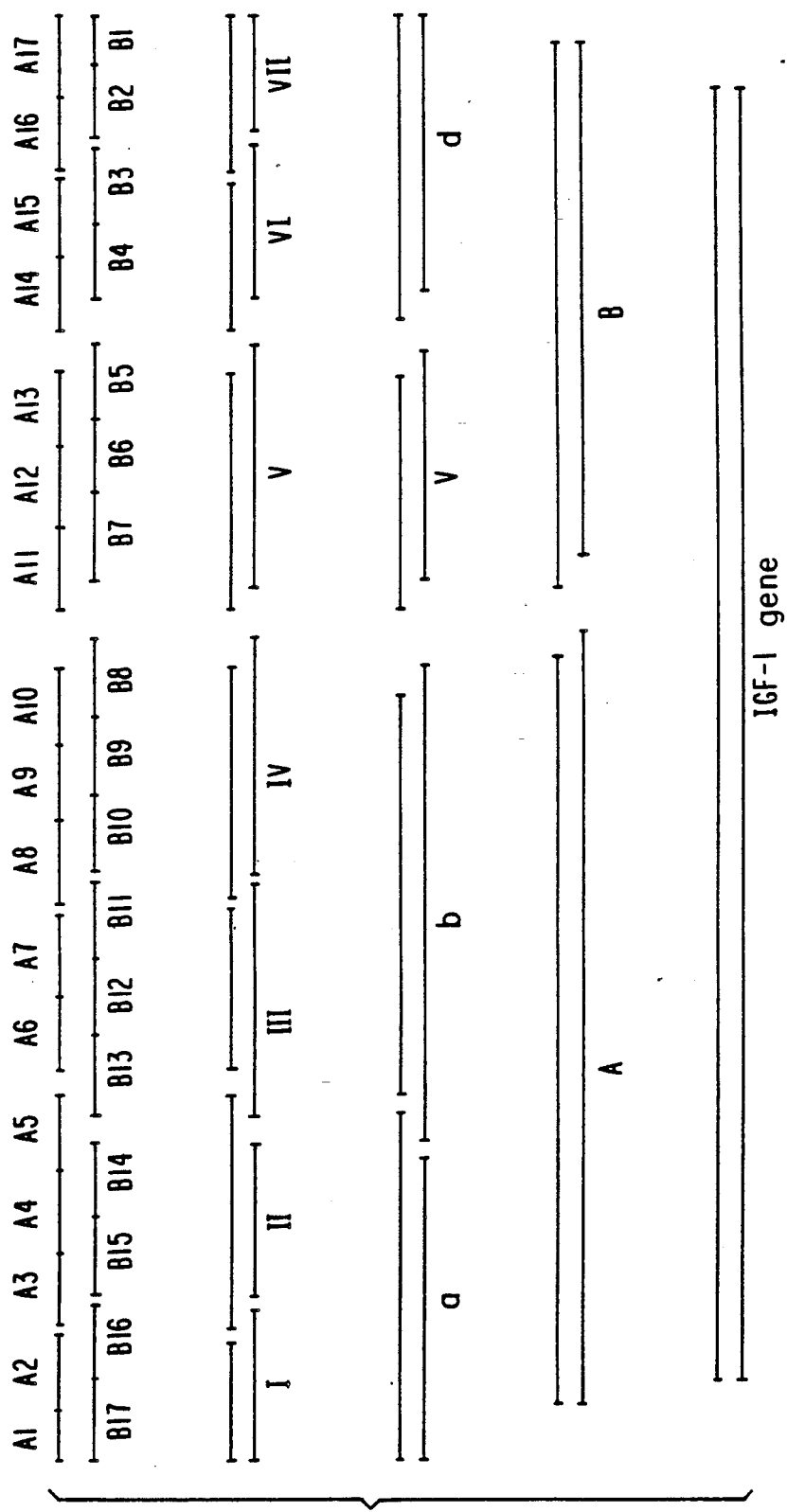
FIG. 21B is a ligation pattern for the IGF-1 gene.

The oligomers shown in FIG. 21A were synthesized on an automatic DNA-synthesizing machine developed by KabiGen AB, Sweden (Chow et al, Nucleic Acids Res. 9, 2807–2817) with N-protected nucleoside chlorophosphites as reagents (Elmblad et al, Nucleic Acids Res. 10, 3291–3301 (1982)). After purification and phosphorylation the oligomers were assembled into seven blocks as shown in FIG. 21B, which were then ligated as also shown in FIG. 21B.

In the last step, block A and block B in FIG. 21B were ligated giving the complete IGF-1 gene. This segment was digested with EcoRI and Hind III restriction enzymes and after purification inserted into plasmid pUC8 and transformed into E. coli JM83. The transformants were screened by colony hybridisation using A15 as probe and one of the positive clones, designated JM83/pKG3, was sequenced, confirming that the sequence matched the IGF-1 gene.

The synthesis of the IGF-1 gene is also described in the Swedish patent application 8303626-9, corresponding to European Patent Application EP-A10 130166 and UK Patent Application publication GB 2142033A and U.S. application Ser. No. 620,400, the disclosure of which is incorporated by reference herein. The DNA-sequence of the IGF-1 gene and the corresponding amino acid sequence appears from FIG. 19, except that a glycine residue (Gly) has been changed into an aspartic acid residue (Asp) as will be described in the following step B.

B. In vitro mutagenesis of the synthetic gene to encode a modified human IGF-1.

Oligonucleotide mediated in vitro mutagenesis was performed on the cloned synthetic IGF-1 gene, in order to change the part encoding the N-terminal amino acid residue of the mature protein. By changing this amino acid residue from a glycine to an aspartic acid residue the dipeptide aspartic acid-proline was formed. This allows for gene fusions encoding hybrid proteins that can be cleaved apart, before or after purification, by formic acid treatment which cleaves between aspartic acid and proline (Landon, Methods in Enzymology 47, 132–145, 1977). Thereby, mature IGF-1, lacking the N-terminal glycine, can be produced.

10 μg of plasmid pKG3 were cleaved with Eco RI and Hind III and a 0.22 kb fragment thereof was cut out from a 5% polyacrylamide gel after electrophoresis. The fragment was eluted and purified as described in the International patent application PCT/SE83/00297 (the disclosure of which is incorporated by reference herein). 50 ng of purified fragment was mixed with 200 ng of phage M13 mp9 and cleaved with Eco RI and Hind III in a total volume of 20 μl. After treatment with T4-ligase the DNA was used to transform E. coli JM83 and the cells were spread on AXI-plates. Cleavage, ligation and transformation were performed as described under Routine Methods. Phage purification from one white plaque was performed as described under Routine Methods. Using the universal primer (BioLabs, New England, U.S.A.) the phage insert was confirmed to be the 220 bp synthetic IGF-1 gene. This phage, designated mp9/IGF-1, was used for the following mutagenesis.

Figures 17, 20:
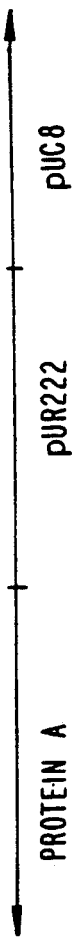
FIG. 20 is a presentation of the nucleotide sequence, and the corresponding deduced amino acid sequence, around the 3'-end of the protein A gene in plasmid pUN202.

Two oligonucleotides were synthesized and purified exactly as described above and in the Swedish patent application No. 8303626-9. One primer oligonucleotide consisting of 24 bases (5'-GTGAATTCTATG-GACCCCGAAACT-3') which was used for the mutagenesis and one probe (P) oligonucleotide consisting of 14 bases (5'-AATTCTATGGACCC-3') which was used to identify successfully mutagenized phage clones. The mismatches between the synthetic IFG-1 gene and the primer are shown in FIG. 17.

16 pmoles of mp9/IGF-1 and 80 pmoles of primer were mixed in a total volume of 80 μl containing 100 mM NaCl, 20 mM $MgCl_2$ and 40 mM TRIS-HCl, pH 7.5. The mixture was heated to 65° C. for 3 minutes and allowed to cool to 23° C. for 30 minutes. After transfer to an ice-bath, 190 μl of $H_2O$ and 30 μl of a solution containing 100 mM $MgCl_2$, 50 mM DTT and 200 mM TRIS-HCl, pH 7.5, were added. 50 units of Klenow fragment (Boehringher-Mannheim, West-Germany) was added and after 10 minutes in an ice-bath the sample was brought to 23° C. for 30 minutes. Another 50 units of Klenow fragment were added and after 60 minutes at 23° C. the polymerase was heat inactivated at 65° C. for 10 minutes. The sample was precipitated once with ethanol, followed by cleavage with Eco RI and Hind III according to Routine Methods above. The 0.22 kb fragment was cut out from a 5% polyacrylamide gel after electrophoresis and the fragment was eluted and purified as described in the above mentioned International patent application PCT/SE83/00297. 50 ng of purified fragment were mixed with 200 ng of phage M13 mp9 cleaved with Eco RI and Hind III in a total volume of 20 μl. After ligation and transformation to E. coli JM83, exactly as described above, white plaques were found in a background of blue plaques. 48 white plaques were further analysed by hybridization with two synthetic probes as described by Winter et al (Nature 299, 21 Oct., 1982). The filters were hybridized at room temperature with $^{32}P$-labelled oligonucleotides and washed at different temperatures. Using probe A2, 5'-ATGGGTCCCGAAAC-3', (Swedish patent application No. 8303626-9), all clones except four showed strong hybridization after wash at 44° C. indicating that these clones contain the original IGF-1 gene. Using probe P, 5'-AATTCTATGGACCC-3', all four of the previously negative clones showed significant hybridization. One of the four phages, designated mp9/IGF-1.M3, was further sequenced using the universal primer as described above. This confirmed a successful mutagenesis as shown in FIG. 17.

200 ng of phage mp9/IGF-1.M3 and 200 ng of plasmid pUC8 were separately cleaved with Eco RI and Hind III. After T4-ligase treatment, in a total volume of 20 μl, the DNA was used to transform E. coli JM83 and the cells were plated out on AXI-plates. Cleavage, ligation and transformation were performed as described above under Routine Methods. Restriction analysis of a white colony revealed the expected plasmid, pUC8, containing a 0.22 kb Eco RI/Hind III insert. This plasmid was designated pKG11 and was used for the following steps.

C. Construction of shuttle plasmid pUN200 containing pKG11

1 μg of pKG11 from step B and 2 μg of pHV14, both digested with Hind III, were mixed and ligated in a total volume of 100 μl overnight at +14° C. After digestion with Eco RV, the DNA-mixture was transformed to E. coli HB101 and plated on LA-plates containing 50 μg ampicillin per milliliter. 52 single colonies were picked to LA plates containing 10 μg/ml of chloramphenicol and 50 μg/ml of ampicillin. After two days at 28° C. one clone appeared and the plasmid in this clone was further characterized by restriction analysis. This revealed plasmid pUN200 schematically shown in FIG. 18. This plasmid, which contains the IGF-1 gene, can replicate both in E. coli and S. aureus.

D. Construction of shuttle plasmids pUN201 and pUN202

Figure 18:
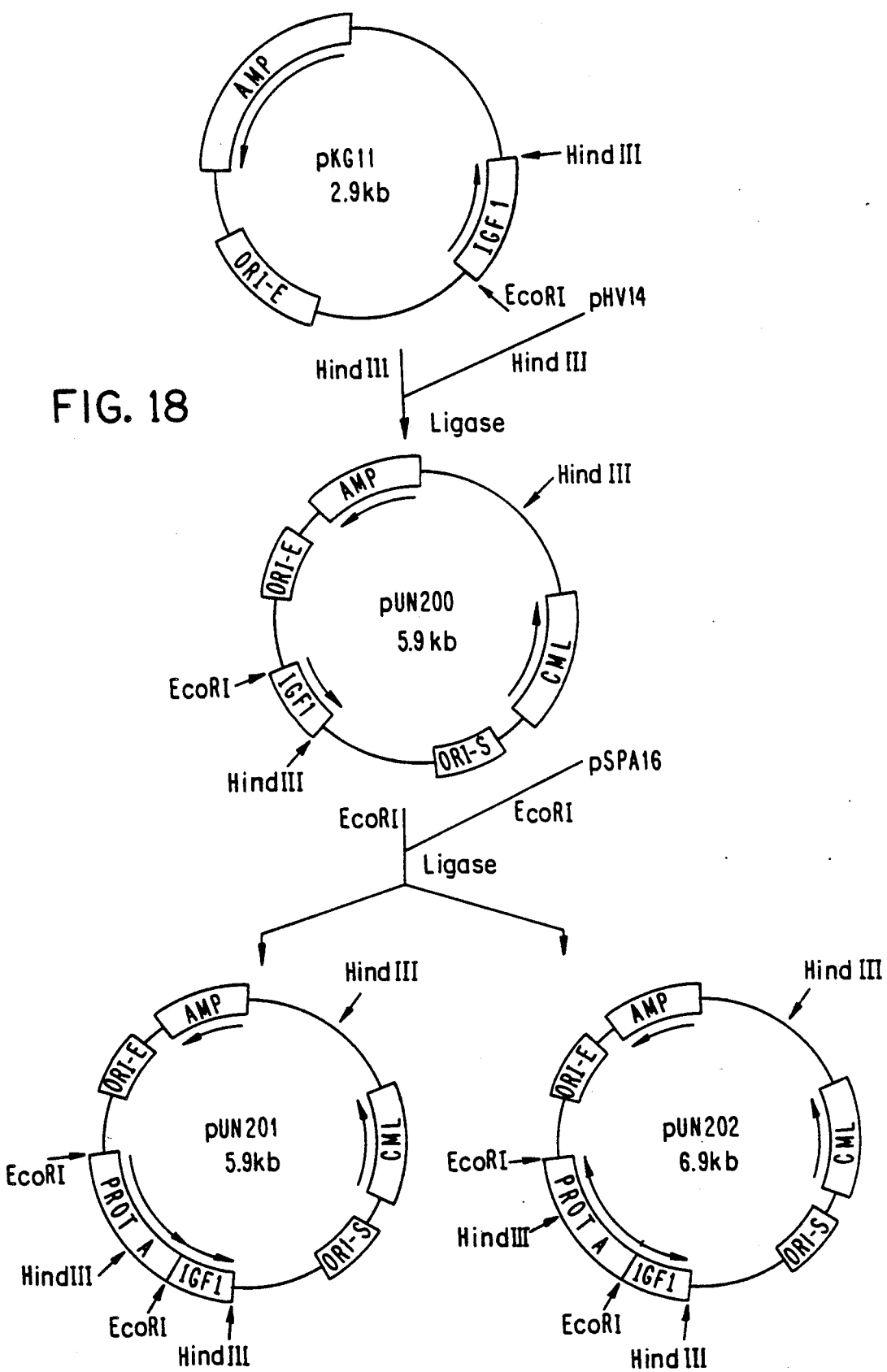

1 μg of pUN200 and 1 μg of plasmid pSPA16, both digested with Eco RI, were mixed and ligated in a total volume of 100 μl overnight at 14° C. The ligase was heat inactivated at 65° C. for 10 minutes. After digestion with Eco RV to decrease the number of background clones containing pSPA16, the DNA mixture was transformed to E. coli HB101 and plated out on LA-plates containing 50 μg of ampicillin per milliliter. Plasmids from 48 clones were analyzed by restriction mapping and 3 thereof were found to contain pUN200 with a 1,1 kb Eco RI insert from pSPA16, corresponding to the 5'-end of the protein A gene. The orientation of the insert in these three plasmids was further analyzed by cleavage with Hind III and two were found to contain a predicted fusion between the genes encoding protein A and IGF-1. This plasmid was designated pUN201 (FIG. 18). The nucleotide sequence and the deduced amino acid sequence of this gene fusion are shown in FIG. 19. The predicted molecular weight of the mature hybrid protein is 38,701.

One of the three clones was found to contain a plasmid, designated pUN202, with opposite orientation of the protein A gene versus the IGF-1 gene (FIG. 18). This plasmid codes for a truncated protein A with a predicted molecular weight of 30,963 (FIG. 20).

II. Transformation of shuttle plasmids pUN201 and pUN202 to S. aureua SA113

10 μg of plasmids pUN201 and pUN202 from step ID above were used to transform protoplasts of S. aureus SA113 as described by Götz, F. et al, J. Bacteriol. 145, 74–81 (1981) and in the International patent application PCT/SE83/00297 (Step IIIA). Chloramphenicol resistant clones were found after 3 days at 37° C. and these transformants were restreaked on TSA-plates (Trypticase Soy Agar) with chloramphenicol (10 μg/ml). One transformant of the respective plasmid (pUN201 and pUN202) was chosen for further analysis. Restriction mapping of the purified plasmids revealed that the intact plasmid had been introduced into the S. aureus SA113 host.

III. Quantification and localization of the protein A activity from clones carrying pUN201 and pUN202

E. coli cells carrying pUN200, pUN201 and pUN202 respectively (from Step IC and D above) and S. aureus cells carrying pUN201 or pUN202 were cultivated in 200 ml of liquid medium overnight. E. coli strains were grown in LB medium with ampicillin (50 μg/ml) and S. aureus strains in TSB (Trypticase Soy Broth) with chloramphenicol (10 μg/ml). The cells were pelleted by centrifugation at 6000 rpm with a Sorvall GSA-rotor for 10 minutes and the supernatant, designated medium, was saved. The cell pellet was washed in 10 ml of PBS+TWEEN and again centrifuged as above. This time the cell pellet was resuspended in 10 ml of a protease inhibitor buffer (0.02M potassium phosphate, pH 7.5, 0.1M NaCl, 0.5% sodium deoxycholate, 1% Triton X-100, 0.1% sodiumdodecyl sulfate (SDS), and 1 mM phenylmethylsulfonyl fluoride (PMSF)). The cells were then sonicated in a MSE sonicator for 4×40 sec. on an ice-bath and centrifuged at 15,000 rpm (Sorvall SS-34 rotor) for 10 min. The supernatant, designated cell extract, was collected and the ELISA-test described under Routine Methods was performed to determine the amount of protein A in the samples. The results are shown in the following Table 4.

TABLE 4

Amount of protein A per ml of sonicated cell culture determined by the ELISA-test. Zero-values correspond to less than 0.1 μg/ml.

| Host (Plasmid) | Cell extract (μg/ml) | Medium (μg/ml) |
| --- | --- | --- |
| E. coli HB101 (pUN200) | 0 | 0 |
| E. coli HB101 (pUN201) | 2 | 0 |
| E. coli HB101 (pUN202) | 2 | 0 |
| S. aureus SA113 (pUN201) | 0.2 | 5 |
| S. aureus SA113 (pUN202) | 0 | 5 |
| E. coli HB101 | 0 | 0 |
| S. aureus SA113 | 0 | 0 |

Table 4 shows that in both E. coli and S. aureus the amount of protein A produced is not influenced by the orientation of the fragment containing the protein A gene (plasmid pUN201 versus pUN202). Thus, the protein A IGF-1 hybrid protein encoded by pUN201 is produced at approximately the same level as the truncated protein A encoded by pUN202. Both proteins are, as expected, found in the cell extract of E. coli and in the medium of S. aureus.

IV. Purification of IGF-1 by IgG-affinity Chromatography and Formic Acid Treatment The media of S. aureus SA113 carrying pUN201 and pUN202 respectively, from Step III, were each passed over an IgG-Sepharose ® 4B column (Pharmacia AB, Uppsala, Sweden) (Hjelm et al, FEBS Lett. 28, 73–76 (1972)) that had been equilibrated with a sodium acetate buffer (0.1M sodium acetate, 2% NaCl, pH 5.5). The column was then washed with the same buffer as above and the adsorbed protein A eluted with a glycine buffer (0.1M glycine, 2% NaCl, pH 3.0). The eluted fraction was dialyzed against distilled water and thereafter lyophilized in two aliquots. The protein pellet of one of the aliquots was analysed on a 13% SDS-polyacrylamide gel at 100 V for 12 hours. The gel was stained with amidoblack (0.1%, in 45% methanol, 10% acetic acid). This revealed a major protein with the molecular weight of 38,701 for pUN201 and 30,963 for pUN202. This is in accordance with the predicted sizes deduced from the DNA sequences (see Step ID above).

The second aliquot was resuspended in 0.5 ml of 70% formic acid and further incubated at 37° C. for 2 days. This process cleaves proteins at the dipeptide sequence aspartic acid-proline. The predicted degradation products from the hybrid protein encoded by pUN201 were, apart from the IGF-1 moiety lacking the N-terminal glycine, five oligopeptides of the molecular weights of 6800, 6600, 6600, 6600 and 600. SDS-polyacrylamide electrophoresis, as described above, also confirms that the major protein bands are shifted from approximately 38000 to several bands around 7000.

The formic acid treated proteins were lyophilized and resuspended in distilled water. The sample from pUN201 was passed over an IgG-Sepharose ® 4B column as described above. The flow through and the eluted material (with the glycine buffer) were saved for further analysis.

V. Analysis of the Protein Products by Radio Receptor Assay (RRA)

The radio receptor assay (RRA) was performed according to Hall et al, J. Clin. Endocrinol. Metab. 48, 271–278 (1974) using a particulate fraction of human placental membrane as matrix. The standard used in the assay consisted of pooled normal human serum having a potency of 1 unit (U) of IGF-1 per ml. The lower limit of the assay was 10 mU per ml. The peptide used for labelling was purified from Cohn fraction IV to a specific activity of 500 U/mg protein (according to RRA). Labelling of the peptide was performed according to Thorell et al., Biochem. Biophys. Acta 251, 363–369 (1971). Purification of the tracer was done on a carboxymethyl cellulose column using an elution gradient of 0.1M NH4OAc from pH 4.0 to pH 6.8. The specific activity of the tracer was approximately 20 μCi/μg. The assay was performed as follows:

The standard or unknown sample respectively (100 μl) was incubated together with 100 μl of placental membrane and 100 μl of labelled IGF-1 overnight at +4° C. After centrifugation the pellet was washed once and counted in a gamma counter. The sample potency was calculated using an "in house" computer program.

Samples before and after the formic acid treatment, from Step IV above, were analyzed by the RRA-test and the results are shown in Table 5 below.

TABLE 5

Radio receptor analysis (RRA) for IGF-1 activity in growth medium from S. aureus SA113 (pUN202) and S. aureus SA113 (pUN201) after isolation and purification by IgG affinity chromatography. Zero corresponds to less than 1 U/l medium.

| Plasmid | Treatment | Activity/l (U/l) |
| --- | --- | --- |
| pUN202 | Before treatment with formic acid | 0 |
|  | After treatment with formic acid | 0 |
| pUN201 | Before treatment with formic acid | 0 |
|  | After treatment with formic acid | 143 |
|  | Flow through,* | 106 |
|  | Eluate,* | 19 |

*A formic acid treated sample was passed over an IgG-Sepharose ® column and the activity was measured for bound (eluate) and not bound (flow through) IGF-1.

From Table 5 it appears that the hybrid protein encoded by pUN201 has no detectable IGF-1 activity. Treatment with formic acid yields IGF-1 activity, and most of this activity does not bind to the IgG affinity column indicating a successful cleavage between the protein A and the IGF-1 moiety.

While embodiments of the invention have been presented above, the invention is, of course, not restricted thereto, but many variations and modifications are possible without departing from the scope thereof as defined by the subsequent claims.

We claim:

1. A method of producing and selectively isolating a desired protein or polypeptide as a fusion product, characterized by the steps of
   constructing a recombinant vector comprising a DNA sequence coding for said desired protein or polypeptide in correct reading frame with a DNA sequence coding for an IgG-binding protein A or polypeptide fragment thereof, capable of binding to the constant region of IgG, such that said DNA sequences together code for an IgG-binding fusion product
   transforming a compatible host with said recombinant vector,
   culturing the transformed host in a suitable growth medium to produce said fusion product,
   selectively isolating said fusion product by adsorption to an IgG-supporting carrier material, and
   optionally desorbing said fusion protein or polypeptide fusion product from the IgG-supporting carrier.

2. A method according to claim 1, characterized in that the fusion protein or polypeptide comprises a unique cleavage site between the desired protein or polypeptide and said IgG-binding protein A or polypeptide fragment thereof, said cleavage site not being present in the desired protein or polypeptide and may or may not be present in the IgG-binding protein A or polypeptide fragment thereof, and that said desired protein or polypeptide is cleaved off from the rest of the fusion product either while the latter is adsorbed to the IgG-supporting carrier or after desorption.

3. A method according to claim 2, characterized in that said unique cleavage site is an amino acid sequence susceptible to cleavage by a cleaving agent selecting from the group consisting of proteases, hydroxylamine, cyanogen bromide and formic acid.

4. A method according to claim 1, characterized in that said recombinant vector is constructed by providing an expression vector comprising a functional DNA sequence coding for said IgG-binding protein A or polypeptide fragment thereof, and a multilinker sequence located before any stop codon of said sequence; and inserting a DNA sequence coding for the desired protein or polypeptide into an appropriate restriction site of said multilinker sequence, and optionally inserting a DNA sequence coding for a unique cleavage site between the DNA sequence coding for the desired protein A or polypeptide fragment thereof, and the DNA sequence coding for the IgG-binding protein or polypeptide, said cleavage site coding sequence may or may not being provided in the expression vector or in the junction end of the desired protein or polypeptide coding DNA sequence before the insertion thereof into the expression vector.

5. A method according to claim 1, characterized in that said desorption of the fusion protein or polypeptide from the IgG-supporting carrier is effected by subjecting the carrier to low pH conditions, high salt concentrations, chaotrophic ions or to competitive protein elution with an excess of soluble protein A or IgG or fragments thereof.

6. A recombinant vector, comprising a DNA sequence coding for an IgG-binding protein A or polypeptide fragment thereof, capable of binding to the constant region of IgG, in correct reading frame with a DNA sequence coding for a desired protein or polypeptide such that the combined sequences together code for a fusion product between said IgG-binding protein A or polypeptide fragment thereof and said desired protein or polypeptide, wherein said fusion product has IgG-binding activity.

7. A recombinant vector according to claim 6 characterized in that the DNA sequence encoding protein A or polypeptide fragment thereof extends from the 5'-end of the combined DNA sequence for coding said fusion protein or polypeptide, said protein A coding sequence may or may not comprising the promoter and signal sequence of the structural protein A coding gene.

8. A recombinant vector according to claim 6, characterized in that a junction between said combined DNA sequences comprises a DNA sequence coding for a unique cleavage site, which is not present in said desired protein or polypeptide and may or may not be present in said IgG-binding protein A or polypeptide fragment thereof, and which may be cleaved by a cleaving agent.

9. A recombinant vector according to claim 8, characterized in that said cleavage site is an amino acid sequence susceptible to cleavage by a cleaving agent selected from the group consisting of proteases, cyanogen bromide, hydroxylamine, and formic acid.

10. A recombinant vector according to claim 8, characterized in that it is a plasmid.

11. A recombinant vector according to claim 6, characterized in that it is a plasmid.

12. A recombinant vector according to claim 7, characterized in that it is a plasmid.

13. A host organism transformed by a recombinant vector of any one of claims 6, 7-8, 9 or 10-12, characterized in that it is a strain of Escherichia, Bacillus or Staphylococcus.

14. A method of producing and selectively isolating a desired protein or polypeptide, characterized by the steps of
    constructing a recombinant vector comprising DNA sequences, linked in correct reading frame, coding for said desired protein or polypeptide, a unique cleavage site and an IgG-binding protein A or polypeptide fragment thereof, capable of binding to the constant region of IgG, such that said DNA sequence together code for an IgG-binding fusion product, comprising a unique cleavage site between the desired protein or polypeptide and the IgG binding protein A or polypeptide fragment thereof,
    transforming a compatible host with said recombinant vector,
    culturing the transformed host in a suitable growth medium to produce said fusion product,
    selectively isolating said fusion product by adsorption to an IgG-supporting carrier material, and
    cleaving off the desired protein or polypeptide from the rest of the fusion product either while the latter is adsorbed to the IgG-supporting carrier or after desorption.

15. A method according to claim 1, wherein the desired protein or polypeptide is subsequently further purified by gel filtration or ion exchange techniques.

16. A method according to claim 1, wherein the desired protein or polypeptide to be isolated as a fusion product with the IgG-binding protein A or polypeptide fragment thereof is selected from the group consisting of transferases, hydrolases, lyases, isomerases, ligases, insulin, ACTH, somatostatin, prolactin, placental, lactogen, melanocyte stimulating hormone, thyrotropin, parathyroid hormone, calcitonin, enkephalin, angiotensin, fibrinogen, fibronectin, prothrombin, thromboplastin, globulin, heparin, oxytocin, albumins, actin, myosin, hemoglobin, ferritin, cytochrome, myoglobin, lactoglobulin, histones, avidin, thyroglobulin, interferon, transcortial kinins and peptide antigens for use in making vaccines.

17. A recombinant vector according to claim 6, wherein the desired protein or polypeptide is selected from the group consisting of transferases, hydrolases, lyases, isomerases, ligases, insuling, ACTH, somatostatin, prolactin, placental lactogen, melanocyte stimulating hormone, thyrotropin, parathyroid hormone, calcitonin, enkephalin, angiotensin, fibrinogen, fibronectin, prothrombin, thromboplastin, globulin, heparin, oxytocin, albumins, actin, myosin, hemoglobin, ferritin, cytochrome, myoglobin, lactoglobulin, histones, avidin, thyroglobulin, interferon, transcortial kinins and peptide antigens for use in making vaccines.

18. A method according to claim 14, characterized in that said unique cleavage site is an amino acid sequence susceptible to cleavage by a cleaving agent selecting from the group consisting of proteases, hydroxylamine, cyanogen bromide and formic acid.

19. A method according to claim 1, wherein the desired protein or polypeptide to be isolated as a fusion product with the IgG-binding protein A or polypeptide fragment thereof is selected from the group consisting of enzymes, hormones, serum proteins, coagulation factors, complement factors, and plasma proteins.

20. A recombinant vector according to claim 6 wherein the desired protein or polypeptide to be isolated as a fusion product with the IgG-binding protein A or polypeptide fragment thereof is selected from the group consisting of enzymes, hormones, serum proteins, coagulation factors, complement factors, and plasma proteins.

* * * * *